United States Patent
Jacobs et al.

(10) Patent No.: US 9,637,749 B2
(45) Date of Patent: May 2, 2017

(54) ***MYCOBACTERIUM TUBERCULOSIS* ΔESX-3 MUTANTS**

(71) Applicant: ALBERT EINSTEIN COLLEGE OF MEDICINE OF YESHIVA UNIVERSITY, Bronx, NY (US)

(72) Inventors: William R. Jacobs, Pelham, NY (US); JoAnn M. Tufariello, Hastings On Hudson, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 65 days.

(21) Appl. No.: 14/399,557

(22) PCT Filed: May 10, 2013

(86) PCT No.: PCT/US2013/040559
§ 371 (c)(1),
(2) Date: Nov. 7, 2014

(87) PCT Pub. No.: WO2013/170154
PCT Pub. Date: Nov. 14, 2013

(65) Prior Publication Data
US 2015/0140038 A1    May 21, 2015

Related U.S. Application Data

(60) Provisional application No. 61/645,391, filed on May 10, 2012.

(51) Int. Cl.
| | | |
|---|---|---|
| *C12N 15/74* | (2006.01) | |
| *A61K 39/04* | (2006.01) | |
| *C12R 1/34* | (2006.01) | |
| *A61K 39/00* | (2006.01) | |

(52) U.S. Cl.
CPC ............. *C12N 15/74* (2013.01); *A61K 39/04* (2013.01); *C12R 1/34* (2013.01); *A61K 2039/522* (2013.01)

(58) Field of Classification Search
None
See application file for complete search history.

(56) References Cited

U.S. PATENT DOCUMENTS

| | | |
|---|---|---|
| 7,722,861 B2 | 5/2010 | Jacobs et al. |
| 7,758,874 B2 | 7/2010 | Jacobs, Jr. et al. |
| 8,084,041 B2 | 12/2011 | Jacobs et al. |
| 8,591,918 B2 | 11/2013 | Jacobs, Jr. et al. |
| 2004/0254349 A1* | 12/2004 | James ................... C07K 14/35 530/350 |

FOREIGN PATENT DOCUMENTS

WO    2010132112 A2    11/2010

OTHER PUBLICATIONS

Serafini et al. Journal of Bacteriology, Oct. 2009, vol. 191, No. 20 p. 6340-6344.*
PCT International Search Report and Written Opinion, dated Sep. 30, 2013 in connection with PCT International Application No. PCT/US2013/40559, 14 pages.
Siegrist M et al., entitled "Mycobacterial Esx-3 Required for Mycobactin-Mediated Iron Acquisition," PNAS, Nov. 3, 2009, vol. 106, No. 44, pp. 18792-18797.
Tufariello J M, et al, entitled "Separable roles for *Mycobacterium tuberculosis* ESX-3 effectors in iron acquisition and virulence," Proc Natl Acad Sci U S A. Jan. 19, 2016;113(3):E348-57. Epub Jan. 4, 2016, 10 pages.

* cited by examiner

*Primary Examiner* — Oluwatosin Ogunbiyi
(74) *Attorney, Agent, or Firm* — Amster, Rothstein & Ebenstein LLP

(57) ABSTRACT

Isolated mutant *Mycobacterium tuberculosis* bacteria comprising a deletion in the ESAT-6 gene cluster region 3 (esx-3 region) are provided, as well as compositions comprising such, methods of production thereof and methods of use thereof.

5 Claims, 9 Drawing Sheets

```
                         SEQUENCE LISTING

<160> NUMBER OF SEQ ID NOS: 5

<210> SEQ ID NO 1
<211> LENGTH: 38
<212> TYPE: DNA
<213> ORGANISM: ARTIFICIAL SEQUENCE
<220> FEATURE:
<223> OTHER INFORMATION: PRIMER DIRECTED TO M. TUBERCULOSIS SEQUENCE

<400> SEQUENCE: 1
ttttttttcc ataaattggt ggcggcgggg ctggactc                          38

<210> SEQ ID NO 2
<211> LENGTH: 41
<212> TYPE: DNA
<213> ORGANISM: ARTIFICIAL SEQUENCE
<220> FEATURE:
<223> OTHER INFORMATION: PRIMER DIRECTED TO M. TUBERCULOSIS SEQUENCE

<400> SEQUENCE: 2
ttttttttcc atttcttggc cacgcctccg ctgtctcctt c                      41

<210> SEQ ID NO 3
<211> LENGTH: 41
<212> TYPE: DNA
<213> ORGANISM: ARTIFICIAL SEQUENCE
<220> FEATURE:
<223> OTHER INFORMATION: PRIMER DIRECTED TO M. TUBERCULOSIS SEQUENCE

<400> SEQUENCE: 3
ttttttttcc atagattggg gctgcactgg cctactccta c                      41

<210> SEQ ID NO 4
<211> LENGTH: 41
<212> TYPE: DNA
<213> ORGANISM: ARTIFICIAL SEQUENCE
<220> FEATURE:
<223> OTHER INFORMATION: PRIMER DIRECTED TO M. TUBERCULOSIS SEQUENCE

<400> SEQUENCE: 4
ttttttttcc atcttttggg cgccagcggt ggagtgcatt g                      41

<210> SEQ ID NO 5
<211> LENGTH: 50725
<212> TYPE: DNA
<213> ORGANISM: ARTIFICIAL SEQUENCE
<220> FEATURE:
<223> OTHER INFORMATION: SEQUENCE DERVIED FROM TM4 BACTERIOPHAGE
<220> FEATURE:
<221> NAME/KEY: misc_feature
<222> LOCATION: (34574)..(34574)
<223> OTHER INFORMATION: n is a, c, g, or t

<400> SEQUENCE: 5
ctcgcggcat aggcagccct ctctcgccag cgttttttcc accagcaaac accggccggt     60
catcccggct acgtcgccac accaccagga ggcagacaca tggaccccga gctgatgcgc    120
gcccgcctcg atgcggtcgc cctcgcgatc cgcgccgccg agctgggcct gctggccgac    180
ggcaagacgg tgctcgactc ggcccgcgac attgccgcgt tcgtcgaggg ttgacatgcg    240
```

```
cgcccccgac atgctcagcg tgcagtgccc tggctgcgcc cgccggtcg agtgcacgat      300 cacgaccgag ccggtggagc ccgagcccgg cgacacgcac gccaagatcc gcgtgcgcgc      360
ggtcgatctg cgcgagcggt tccgcgccca tctcgtcgag tgcactcgca ccccgaggc      420 tgtgctggcg gtggcttatg gcggttaagt ctgtcgccgc cgcggcggcc gacggcgacc      480
ggcgcgagct gctcgtcgcg atgcgcgccc gcgtggcgac cgcggttgaa gatcccgaga      540
cacctgcccg cgatctggct gccctgacgc ggcggctgtt ggagattgcc aacgagattg      600
cggcgattga cgctcaggcc gagcagggcg agggcagcgt cgccgccgcg gcagcgacgc      660
ccgatgaacc attcgacggc gacgcttagc gaggtcgcgc gccacgtcat tgcgccgcaa      720
ggcatcgtgt cgacggcctg gccgtcggtg cgcgcgacgt gtggcgcgat gggcctcggg      780
ttcgacctgt ggcaggacga cctcggcaag ctgatttgcg cgaagcgcga cgacggcctg      840
tacgcggccg acatgttcgc aatgtcgatc ccgcggcaga ccggcaagac gtacctgctc      900
ggcgcgctcg tgttcgcgct gtgcatcaag acgcctaaca cgacggtgat ctggacggcg      960
caccggaccc gcacggccgc agagactttc cgcagcatgc agggcctcgc gaagcgcgac     1020
aagatcgccc cgcacatctt gaacgtgcac accggcaacg gcaaagaggc cgtgctgttt     1080
aagaacggct cgcgcatcct gttcggtgcc cgcgagcgcg ggttcggccg tgggttcgcc     1140
ggtgtcgacg tcctgatttt cgacgaggcg cagatcctca ccgagaacgc gatggacgac     1200
atggtgcccg cgacgaacgc ggcgcctaac ccgctgatcc tgctggccgg tacgccaccg     1260
aagccgacgg accccggcga ggtgttcacg gtgatgcgcc tcgacgccct ggcgggcgac     1320
gtcgacgacg tcgggtacgt cgagatttcc gccgacgagg acgccgaccc cgacgaccgc     1380
tcgcagtggc gcaagatgaa tccgagctac ccgcaccgga cgtcggcccg agcgatcctg     1440
cgtatgcgta aagcgttggg cgatgagagc tttaagcgcg aggcgatggg catatggccc     1500
aaggtcagcg tgcaccagcc ggtcgtgaag tcggggcggt ggcacgacct gttcgacctc     1560
ggccccgagg acggcgaagc gcctaacgcc ctggcggtcg acatgtcgca cggcctggcg     1620
atttcggtcg gcgcgtgctg gctgatggac gacgacggcc gccacgtcga ggaggtgtgg     1680
gccggtaccg acaccgcggc ggcggtcgac tggatcgctg agcgggccgg gcggcgcatc     1740
ccggtgctga tcgacagcat gagcccggcg gcggcgctgg cgcccgagct gaaagcccgc     1800
aaggtcaagg tgaagctgac cggcgcggcc gatatggcga agggctgcgg cctgtttgag     1860
aacggcgtca acgccgacac gttgacgcat ggcgatcagc ccgcgctgaa tgacgccctc     1920
gctggcgccc gtaaacgccc gatccgcgac gcaggcggtt ggggctggga ccgccgcgac     1980
ccgacctgcg taatccatcc attagtggcc gtgacgctgg ccctgctcgg tgccgccgac     2040
ggccgccgtc gccgagctgg ccgcggtggc ggcgccatgt tcgtgtgaga ggggggggcc     2100
gtgactgttc ctgttgacgt gatcgccgac gccccagcgg ccgacgtgga gttccccgag     2160
gactcgatga gccgcgagca gctcggcgcc ttggtcgccg acatgtggcg gctgcatatt     2220
tccgagcgtc agtggctcga ccggatttac gagtacacca aggggctgcg tgggcgcccc     2280
gaggtgcccg agggcgccag cgacgaagtc aaggaactgg cgaagctgtc ggtcaagaat     2340
gtgctttcgc tcgtcgtga ttcgttcgcg cagaacttga gcgtggtcgg ctaccgcaac     2400
gccctggcga aagagaacga ccccgcctgg gagatgtggc agcgcaaccg catggacgcg     2460
cgccaggcca aggtgcaccg cccggcgctg acgtacggcg cctcgtatgt gacggtgacg     2520
ccgactgatg aggggccggt gttccgcacg cggtcgccgc ggcagatcct cgccgtgtac     2580
```

-continued

```
gccgacccgt cggtcgacgc ctggccgcag tacgccctcg aaacgtgggt cgcgcaaaag    2640
gatgcgaagc cgcaccggcg cggcgtgctg tacgacgaca cgtacatgta cgagcttgac    2700
ctcggcgagg ttgtgctcgg cgacgcgggc ggcgggcagg ccacgcagca gccggtgaac    2760
gtgcgcgagg tcaccgacgt gatcgagcac ggcgcgacgt tcgagggcaa acccgtttgc    2820
cccgttgtgc gtttcgtcaa cggccgcgac gccgacgaca tgatcgtcgg tgaggtcgcc    2880
ccgctgatcc tgctgcagca ggcgatcaac tcggtgaact tcgaccggct gatcgtgtcg    2940
cggttcggcg ccaacccgca gcgcgtgatc agcgggtgga ccggcagcaa ggccgaggtg    3000
ctcaaggcat ccgcgttgcg cgtgtggacg tttgaagatc ccgaggtgaa ggcgcaggcg    3060
ttcccgcccg cctcggtcga gccgtacaac ctgatccttg aggaaatgct gcagcacgtg    3120
gcgatggtcg cgcagatcag cccggctcag gtcaccggca agatgatcaa cgtatccgcg    3180
gaggccctcg cagccgcgga ggccaaccag cagcgcaagc tcgccgcgaa gcgtgaaagt    3240
ttcggcgagt catgggagca actgctgcgc ctggccgccg aaatggacga cgaccccgac    3300
acggccgccg actcgggcgc cgaggtgctg tggcgtgaca ccgaggcccg ctcgtttggc    3360
gcggtcgtcg acggcatcac caagctggcc tcggcgggca tcccgatcga gcacctgctg    3420
tcgatggtgc ccggcatgac gcagcagacg atccaagcga ttaaggactc gctgcgcggc    3480
ggcgaggtga aatcgcttgt cgacaaactg ctgtcgaacg aaccggcgcc agtgcccccg    3540
ccgccgcccc aggcggctgc tcaggcgctc aacgagggcg cgtgaatgg taacggcggc    3600 gcctgagttt cagggcgtcc tggccgagct gagcgggcgt gcgggtatcg ccgtcgaccg    3660
gctcgtgccc cggctgagcg gcctgaccga ggccgagggg ctgcggttca tcaccgacgc    3720
ctatccggcg ctgatcgacc cgtacctgtc ggcgtcgtcc aagctgacga cgcagtggta    3780
cgccgagcag cccgcccgcc agcaaccgcg cggcaaaagt gccaacgcgc agctcgcagg    3840
cgatttccgc ggtggcccag caaacacgca gggcggcaag ctgtttgtgc cggaaccggc    3900
gccgctgccc gaccctgacc gcctgggtgc taacgcccgg tgggcgctgc tgcagaacga    3960
cccggtggtc gcgctgcaag gctcggcgac ccgcgcggtc atggactcgt cgcggcgcac    4020
ggtgctcgac aacgccaagc gcgagggcgt cggtgggtg cgatacgcct cggtcacggc    4080
gtgcgggttc tgccgcatgc tcgcgacccg cggcgccgtg tacaagtcgg ccgacaccgc    4140
gctgcgttca cacgatcact gcgtgtgcct ggcggtgcca gaccgcaacg gctcgtatca    4200
gccgcccgac tacgtgcagc agtgggagca ggattacctg caggcccgcc gcgacggcct    4260
cactacgccg caagagattt cgcgggcgat ggaggccgcg ggcgagcagc gcaccgcgac    4320
ccggcagtgg ctcaacgccg agaaggcgca ccagcgcaac gtaagcgact ggctcgacgc    4380
cgagttcgtc cacaacaacg ccgtcgacta ctggcagaac gtcgacgccg agctgggcaa    4440
ggcgttcgcc gagcccgcgc cgaaggccga gccgaccgcc gagcccgccg cgaaggccga    4500
gcccgcggag gccccgctcg accggctgct gcgcgaagcg aacgcagcaa tggaaacggg    4560
cgactacgac aaggccgaca gctgctcgc cgaggccgac aagctcgaac gcgcgcagca    4620
agccaaggcg gccaaggcgg ccaaggccga taaggacaag gcccggcgcc aagcggccga    4680
cgccgccaag caagacgagg tgctgaacct cgtcgagcag ggctgggaac cggccgaggc    4740
cgagtctcac gtgtacggca agagtgtcga gtcgatccgg cgccgtgact tcatgtcgca    4800
ggcccgcggc gacggccaca acggcaagtc gttcgacgcg cttgtcggcg acgtgcacgc    4860
cgagatggcg gccgagcagt tctggaaggc cgaggcggcg acgaacgcct acatgctcaa    4920
acgcaagtac gagggcaagg tcgacccgcg caagctgtgg acgatgaacg aggcggcggc    4980
```

```
ccgcaagtac atgtcggagg agatggccgc gtggttcgac cagcacggca ggctcacgag      5040
ggcggcgctg cgcgagtcgg tgctcagcgg taaaggcaac tggcgcaacc cactaacggc      5100
ggatttcctg caatgagcga taacagcgag ctgatcgccg cacgcgacga ggggcgctcg      5160
gcgccggtcg gtgcagtcaa tccgtatgcg gggcagggca tcaaggcccg gctgtggcgc      5220
ctcgggtacc gcacgatgct gctcgacatg ctgaacaact cgcccgctgt gcgggcgtac      5280
ctgcaggcgc agcaatagat ttcacgccca acctgggcgg gtgagcgtgg acggccaacg      5340
cctaatcggc cggtgatgct gacgagctac ggagcaacta acatggcag aacaaactga       5400 gtcgaccacc gaaaccaccg aaggcaagcc cgccgaggac aactcgaccg agggcgccga      5460
cggcggccaa agcggtgacc agggcaagac tttcacacag gccgagcttg acaaggtgat      5520
cgagcagcgg ctcgcccgcg agcgggcgaa gttcggcgat tacgaccagc tcaaggctga      5580
cgccgccgag ctggcaaaga tccgcgacgg cgaaaagagc gagctgcaga aggcgctcga      5640
acgcgccgag caagccgaga gcgcgccga gcaagccgag ttcacttctc tgcgcagcaa       5700
ggtggcggcg gtcaagggcg tgcccgcgtc gtcgctgacc ggcaagaccg aggacgagct      5760
gaacgcctcg gccgacgagc tgatcgcctg gcgtgaccag aacaagccgc cgcaccacc       5820 gaagcgcaac cccgcgcaag gcggcggcgg cctcaagtcc ggtgccaccg gcaacggcaa      5880
caccaattcc gaccccaaag ctgccgcggc agaagcattg cgccgcttac gcgccggggg      5940
ctgacaacag gtttccgcgc gaggaccgac ctcggcggga gaaggagaa agccaatcat       6000 ggctgacatt tcacgcgccg aggtcgcctc gctcatccaa gaggcttact cggacacgct      6060
gctggccgcg gccaagcagg gcagcaccgt cctgtctgcg ttccagaacg tgaacatggg      6120
caccaagacc acgcacctgc cggtgctggc gaccctgccc gaggccgatt gggtcggtga      6180
gtctgcgact gacccgaagg cgtcaagcc caccagcaag gtgacgtggg ccaaccggac      6240
cctcgtcgcc gaggaaatcg ccgtcatcat cccggtgcac gagaacgtca tcgacgacgc      6300
gaccgtggcc gtgctgaccg aggtcgccga gctgggcggc caggcgatcg gcaagaagct      6360
cgaccaggcc gtcatttcg gcaccgacaa gcccgcctcg tgggtttccc cggcgctgat       6420
tccggccgcg gtgactgcgg gccaggccgt cgaggtcgtg ggcggcgtcg ccaacgagtc      6480
cgacattgtc ggcgcgacca accgggccgc gaaggcagtt gcgtcggccg gtgggcacc      6540 tgacaccctg ctgtcgtccc tggcgctgcg ttacgaggtc gcgaacattc gcgacgcgaa      6600
cggcaacccg gtgttccgcg acgactcgtt cgccggtttc cgcaccttct tcaaccgtaa      6660
cggcgcatgg gacgccgacg cggcgatcga ggtgattgcc gacagctcgc gggtgaagat      6720
cggtgtccgt caggacatta cggtcaagtt cctcgaccag gccaccctcg gcaccggcga      6780
gaaccagatc aacctggccg agcgcgacat ggtcgccctg cggctcaagg gcggttcgc       6840 ctacgtgctg ggtgtgagcg cgaccgctca gggcgccaac aagacgccgg tcgccgtcgt      6900
ggcaccggct gcctagtgcg ctatcgccac gccttgacgg gggcggttat cggggtgcgt      6960
gagggcaccc tgctggccgc cctcgtcgag ggcgacgaca actggacccg gtacggaggt      7020
gctagccatg acggagtgca aggcgctggc gacaagccag gacgtcaagc gggcgctgcg      7080
gcgggatctg acggaagcgg agcagacgga cctaagcgag ctgctcgccg aggcaacgga      7140
tctcgtcgtc gggtatctgc acccgtaccc ggtcccgaca ccaacaccgg ggccgatcaa      7200
gcgggtggtg gcgtcaatgg tggccgcggt gctgacccgg ccgacgcaaa tcctgcctga      7260
gacacaatcc ctcaccgctg acgggttcgg cgtgacgttc acgcccggcg gtaactcgcc      7320
```

```
ggggccgtac ctgtcggctg cgctcaagca acggctgcgg ccgtaccgca ccggcatggt      7380
tgcggtcgaa atgggcagcg agcgttactg ctgatgttcc cgacaccgca caaggttgtg      7440
catgtcgacc gagtgaaggt cggcgagaac gcgatgggcc aggcgatcac cgagccgcgc      7500
acccgcaccc gctgggtgac gagtctgcgg ccgagggtga acgagagcgg cactgctgcc      7560
gccctggccg atcgcgtcat cactgagtac acgatggcga cccccgagag tgactggacg      7620
cacggcgacc aagtgaccga tgcgcggggg cgcaagttca aggtgcacgg cgacgtcgag      7680
gactacaacc tcggcccgtt cgggttcacg ccgggctatc gagtgacgtt gcggagggtg      7740
aacgatggcg cgcaaaccgc ttgacatgcc caactcggag caccgcaaga tccgcaagct      7800
gcccgaggtg caggccgagc tgcaacgcct ggcggccgag gtcgcccggc gcgcaggcgg      7860
aatcgccgac gccccgacg gctacggcac cgaccttgag gtcggccgca ctcgtgcccg      7920
cgcgcacgtg tggccgaagt cgagtgcggc gatcaaggcc gaaatcaaga cggcgccgct      7980
tatgacgatc gccgcggagc agggccgca acagtgactc tcgtgccctc tgtcggcccg      8040
ctggtggccg cgcgagccta tctgctcgac gagctggcgg cccgcgctaa cccgctgccg      8100
gtcggcgcca acccgcccga gggcgagccc agctcgtacg cgctgctgtc ccggccgggc      8160
agcgaccgcg acgtgtttct cggccacttc ctgatccgcg tgcgcgtttt cgacagcgac      8220
gtcgtgcgtt tggagcgcaa cgccgatctg ctgcacgcgc tgctgtgcgg ggccaaccac      8280
cgcaaggtgc acacgcccga gggcgacgtg tggatcaccg gcgcggcgca tcactacggc      8340
ccggccgacc tcgacgaccc cgacgtgccg ctgttcggca tgcaggccgc ggtgttctgg      8400
acgatcggcc tcaagcccgc ccgccgtagc taaccgccgg caaaaactcg agcacacccg      8460
ctgacctgcg gcggcgccca attccgcagc gattcaagca aacacaccac cacaccaggc      8520
aagtgtccct cgggccgacc ggctcgcggg tagttagttg cccgcgcggg caagttagga      8580
gagtaagcaa tggcagactc gcccgtcctc gaaaactcgt ggggcgacgt taccaaggtg      8640
ttcgcggcct cgccgtctga cctcgaaacc gttggcggcc tgtggtatgc gccgttcggc      8700
acgccgctgc cgaccgacgt cgacgagccg ctcgacgaca agttcaagaa cctgggcttt      8760
atctcggtcg agggcgtaac cgtcaagatc gacgaccaga ccaagccgat cgaggtttgg      8820
ggtggcgacg aaatcggtgc gctgcgcgac aagttcgcga tcgagtacag catgaagctg      8880
ttccaagtgc tgtcgcccga ggtgaacgcc gccattttcg gcgagggcaa cgtgctcacg      8940
tccgaggcca ccgcgatgca cggcgcccgc atgaaggtgc tcatcaacag caagctgccc      9000
aagcgttgct cgctggtgct cgactcggtg tacgaggaca agatgatccg ccaggtcgcg      9060
cagatcgcgc agaaggcggg cctggctgac ctcaagctgg tgcacaacga gccgatggca      9120
ttcgagccga cattcaaggt gctcaagggc actgacggca accacgtcgt gcagtacagc      9180
gacgacggcg tcatttccgt ctagctgaca cctcacagac cggcaccccg cgcgctttcc      9240
tggtgggggc gcggggtgtc tcaccacatt cacaccaggg cacgccagga aacacaccag      9300
gaggttaaaa gctatggaaa tcaacgcgac tgacacggcc cccgaggtcg acgtcgtcga      9360
gcaccaggac gtcgacgagc cggtggcggc cgaggcgacc cccgaggcgg gcaagacgat      9420
cgccgaggag tgggccgacg agtacgacgc gggcgccgag ctgttctgcg ccacgttcga      9480
cgccgacgat ttcgaccccg agtacggcgt caacgagtac cccgacggca cgaccgtggc      9540
cgtcaagcgg tgcctgcgca agccgccgcc ggggtggatt cgccagcacg cgcacctgtc      9600
cgaccttgag cgcacgttcg cgctgatcga gaagcactgc agcgacaagg ctctcgacat      9660
tctcgacagc ctcgccgaga agccgtggaa tggtttcgtc gaggcgtggg gccgtgacgg      9720
```

```
cgggctgatc gagggaaaat ctcgcaggtc tgcgcggcgg taaggcaagt cgaggacgcg    9780
atccgccggg acatggttct ggcgggtcgc gcttccgacg acgggtcgct cgattgggac    9840
gacctttacg ctttcatttt cgcctcgccg ccgggcaccg cggtgttcca tgcgttcgag    9900
aagggctgga cgacaagcga ttacctgctc gcacacgtga tcgacgccct acggatcaac    9960
aactggcagc gcaccgaggg cgcgcataag aatccgccgc agggcgcacc cgacccgttc   10020
ccgcggccgg cgacgacga cgacgagccg aagcgcgccg agggcgcggt gtcggccggt    10080
atcacggcgg cgaccaggac gacggtcggc aagttcatgg caatgcgcgc tgagcgcgaa   10140
aagcgttggc gcgaaaagca ccagcgagga gaggggggcg taaatgtcag aggccaagta   10200
ttacctgaca atcctccccg agactcgcga gcttgagtcg ggcatccgcg acgcgatgag   10260
ccgcgccgag cgcgggctca aggtcgcccc gaagttcgac acctcgggcg ctcagcgcgc   10320
aggccaggac gcgggcaagg gaatcagccg cggcgtcgat acggccgacc ccggtaaggg   10380
cctgggccga agctggccc gcaacctcgg cgacggttcg cgctcggca agcagtacgg    10440
ctcgcggctg tcggcgggca tcgacagcgc gctgtcggtc gccggtggca tggcgatcgc   10500
caaggttggc agcaagatca cggggcgct cggctcggcg atgcgggccg ggttcggccg    10560
tctgacgcag atcgactcgg cgcagttcaa gctgaaatcg cttggcaatg aggccagcac   10620
ggtcgcctcg gtcatgcagg acgcgaccgc ggcggtgaag ggtacggcgt tcggcctcga   10680
cgcggctgcg accacggccg cctcggcggt ggccgccggt atcaagccgg gcgagcaact   10740
gaccaagtac ctgtcgctga ccgctgacac ggccgcgatc gccggtacga gcctcgacga   10800
aatgggctcg atcttcaaca aggtgcaggg ctcgggcaag gcgatgacgt ggagcttcg    10860
ccagctcgcc gaccgcggtc tgccgatctt ccaatggctg caggacgagt ttcacgtcag   10920
cggcgacgcg ctgcaggaca tggtcgcgca gggcgcggtc gactctgaga ctttccgccg   10980
ggtgatcgag aagaatatcg gcggcgccgc aaagggtatg gcggcagtt tcgttggctc   11040
gatggcgaac atgaaggccg ctatgtcgcg gttcggcgcc gaggttatgg ggccgatctt   11100
taagggcgtg cagccgctcg cgaccgggct tatgggcgtg ttcgacaagc tgaccgccgc   11160
gatcaaggcg cctatgggca acgtgacgac tgtggtcgag cagtgggcca agggcatgtc   11220
ggacaagatg caggcgtggg ccgacggcga cggcatgaaa aaggtcattg acttttcgg    11280
ccgcgtcggc gactcgatca aggctcttgc gaccggcggc gacagcggca agctcggcga   11340
gattgtccag tcgttcaaaa acattgggcc gtcactgcag acggccgggt cgtcgtttgc   11400
ggcgatcggc gccacgctgg ccgcgatcgg ccccgaggtg ctgtcgtcgg tgctcgtgcc   11460
cgcgctgcag ctcgccgccg gggcgctcaa gttcatggcc gacaatgcct cgtgggcggt   11520
gcctacgatc gtcggcctgc gtgtcgccct gttcgcgcac caggccgtgc tgactgcggt   11580
ggcgatcggc accaaggcgt acggcgtcgc gatggccgtg tggtcgggca tcacgaaggc   11640
cgcgaccgcc gcgcagtggc tattcaacgt cgcgctgacc gctaacccga tcgggctgat   11700
tatcgccgcg gtcgtcgggc tcgctgtcgc gatttgggcg ttttttcacga aaaccgaagt   11760
cggccgccaa ctgtggtcga agatttgggg cggcatcaag gccgctgtgc acgtgttcgt   11820
cgagtggttc aagaacacgg ccgtgccgtt catcaaggcc gctgggaca tgatcgcggc    11880
gggggccatg tggttgtggc acaacgtcat cgagccggtg tgggagggca tcaagacggc   11940
gatcaagttc gccattgatt tcatcaaggc cgagattcaa gctgggtgg cgatcttcca   12000
tttcatcgag gacgtgtggc gcggcctggt cgacacggcg catgcggtgt ggcagggcat   12060
```

```
cgtcgacaag ttcaccggcg tggtgaattt cgtcaaggag ctgcccggca agatcacctc   12120
ggccgctaag ggcatgtggg acggcatcaa agacgcattc aagtcgatga tcaacagcct   12180
gatcgacatg tggaacgggc tggccgacaa gatgacgttc accgttcccg acattcccgg   12240
cgtgccccgg cgtggcgaga gcgtgcaccc gatcccgaat atcccgcgcc tggcgaccgg   12300
cggccggatc agcgggccgg gcaccggcac gagcgacagc atcctcgcgc gtatcgctaa   12360
cggcgagttc atcaccaacg ccgccgcgac ggcccgcaat ctgccgctgc tgcaggcgat   12420
caactccggt gcgccgctgt gggagctgat tagggcgctg ccgaggttcg ctggcggcgg   12480
cctggccgcg ggcctggcgt ccgagcagaa cctacagccc aacagcatcc tgatttcgcg   12540
gctggtgtcc aagctgttcc cgcagatcaa gacgattggc ggctggcggt cgcaggacgc   12600 ttacccgat cacccgtcgg gccgggcgct cgacattatg atccccaact actcgtcgaa   12660
ggacggtgtt gcgctgggcg acagcgtgat gcagttcctt atgaagaacg ccgacgcgct   12720
cggcgtcgag tacacgatct ggcggcagac ctaccgcaac acctcggggc agtcgaacct   12780
catggaggac cgcggcagcg acacgcagaa ccacatggat cacgtgcacg tgacgtcgaa   12840
gggcggcaag ccgaagggcg gcgtggacac cgcaccggcg ggcctgtctt gccgtctgg   12900 cgtcaacgtg agcggcctcg acggcgtggg ggtgcctagt ggtggctcgt cggcgctcgg   12960
cagtgccacg tcggcgtctg gcggctcgta ccgggcggcc accgacgacg agcttaaggc   13020
gtcgtcgggc aaggtcgaca gcgcccgcac gtcgctgcgc aacgccgaca aggctatcga   13080
ggacaagcag tacgcgctcg acaaggcgaa gcgtgacctc gaaatcctca agggtaagaa   13140
gcacaccgcg gcgcagcttg aggacgccga gcaccgcgtg cagaaggccg agcgcgacct   13200
ggccgacgcg atcgagaagc gcggcaaggt caacgacaag ctgaccgacg ccgagcaggc   13260
cgacagcgat ctgcgcacca agggcaaggc caccaagggc aagtcgaaag acggcaaggg   13320
cggcggcctc gacggcagcg acctgggcaa gacgttcgtg tcgggcatgc tcgaaagcat   13380
tggcctcgac gggtcgctgt tctcgaatcc gtttgagtgg ccgacggtta agtcggcgct   13440
cgccggtgtg aactacctcg gcaacctgct gtcgggcaag ggccgcgacg gcgaggaggg   13500
caccaccgac agccccggcg ggttcgccgg tggagtcgct gacagcgtcg gcctgggctc   13560
gctgttcaag ggcctgggca gcccgatcga cgggcaggac gtcggctggt cgccgcagtc   13620
tggcagcccc gcgctggcac cgggtgagtt caacccggcc accgtcggcg gcggctcggt   13680
cgccgagggc gccgtcgacg ctatgtcggc gttcgtcccg agcgcggccc aggcggcgca   13740
gggcgatcag cctgcgcagg ttgacaactc gatcaacatt tcggggccgg tcggtatgga   13800
cccggtcgcg ctgcgctcgc agatccacag cgagcagaac gcccgcaccc gctccacggt   13860
tcggcgcgtc tagctaacgg ccggcagcc gccgattcat gccttgagct gcggcggctc   13920
gtcgagccag ctaacaactt ctatctatgt gaggcggtga agcgcggtca tgtcttggat   13980
gcacgacgat ttctggctcg acccgcccaa gtatccgaat gactggcagg caacccggc   14040 gtaccccgag gagaatccgg cgcacccgca ctttcagcgg atgggcgcct ggcacgacct   14100
cggtaagaac ggcgagtacc tgcggtcgac ggcgaccaag tggtattact gccacccatc   14160
taacggcaag gtgtggcacc tcgccggggcc gggccgcggg cgtgagggcg tcgtgatggc   14220
gcgcgagctt gagggcgtca tgcagcccga tttcgagatc cgttggagtg agggcgctta   14280
cacgatcggc gccaagcccg agcgcgtcga ctataaaaag cggcgcatca acctgggcgt   14340
ggcgattcag cccaacctca acgcggagcg gatcgaggag cctaattcgt tctcgtaccg   14400
catgatcgag gactcgtggt ggtcgtcgtg gtctgagact gtgcccggtt tcctgggctc   14460
```

```
gttcacgcgc acgcatgggt tccgttggct gcgtgtgctg ctcggcgagg ccactaaggg   14520
cgcgctgtcg atcgacccga cgggcaacga caacaactcg gtgattcaca acatggcggt   14580
cgacgccgcc tggccgttct acgccaagcg cccgctcaag cgtgtgtgga aggtcaaccc   14640
ggccgacgtg tacgcgaagg gcaaggccga gggcgttatc gcgatcgcga accgcggcac   14700
gtgggagtcg tggccgaagt tcctggtgcg cgggtctggc gaggtgtgga ttcaggacgg   14760
catcgagggc cggatggtca agctgcccaa gctgtatgac accgacggct cgtacatgat   14820
ggtcgacacc gacccgacgg cgcgcacgat cacgaccgag aaagatccgg tcgacggcca   14880
gctctacaag tacctgcgca acagccaact gctcgacctg ctgctgcacg acgtgacggc   14940
tgcgcggcta ccggcgcagc ggcgcatccc cggtggtatc ggtttcgacg gcaagatccc   15000
gccgcgcacg gtggcgcaca tcaaggtgtc gcacaccaac ccgcagggct caatcacgtg   15060
catcatgccg cagtattacc ggatggcgtg gtcgtgacgg cgacgctgtt ggagcccccg   15120
cggatcggcg tcaacggggc gcctgaccct gtgcgcgacc cgattgccgc gtacacctac   15180
ctcgacgcgc gccgcgaggt gatcgacgag gaggcccgcg cccggccgct cattcgcttg   15240
tgggacaagc aaatgcagta cataggcacg gtcgccgccg agaagtcggt cgacgccgag   15300
gagatgttgc acgacaccgg caccggcgac attgtgctgc gcggcgacga ctggctcgtc   15360
gagttcatgc gctcggacgt gcgcaaagac gaggatctgc acatcacgat cgacccgtac   15420
ccgcaccggc gtaactggcg gtggcggtgg aacgcgaagg tcactaacgt gcgcgtgaag   15480
cgcggcgagg atggtctgcg cacggtcacg cttgagtgct cgcacaatcg ggagcattgg   15540
aagcacatct atttcggcgc aacgcctttc agcccgccgg aggtgcagcc gattcgcgcc   15600
tggctgctgc cgggcaacac tcggaccatt atcgcgacaa cgggtttcat caacctggcg   15660
cgtaattaca acccgctgct ggcgttgccc acgcaggtga tgaatcccgg cgcgtggctc   15720
ggcgaggcca gcaatgtgct gaacctcaac ccgttaaatt ggcctgtcca aatgcaattc   15780
gtcaatccgg tgttcgacca gtcgcgcttt agcgtgatca tgtcgcgctg ggctgacgcg   15840
cacagcgtca ccgaggcgat gctgaaagac gcgggctgca acgtgcgcgc gtacatgtgg   15900
ctgcccgagg acgaggacag cccgcacccc gagctggccg cgattatcgg tgagaaggcc   15960
gcccggccga ctcgcgcctg cattgtgctt gcggtggagg acaattcggg ccgcactggc   16020
tggtccggta cggccgccga cggtttcatg cagcttatcg cgtcactgg cgacgacatg   16080 atccgcgagg tcgtcgggca gatcgacgac aagggccgga ttatcgaccc gataaccaag   16140
gcaacgcttt tcggcaagct gctgggcacc gccccgtcga tcccgagtgt ggtattccgc   16200
gacaccgagc actcgtcgat catcacggcc gagcactcga tgttccgtgc gaaggcccaa   16260
aaaatcctga caggcggaaa atcacccggc tgggttaacc aaactcagac cttcctgatc   16320
cgatatgcgt tgtcgcagtt ggctcaagtg gtgttcgcta ctgagcaacc cggcgccgag   16380
ggcttggaca acctctatca gggccaggcc gacgacacgc tgatggcgtt catcgcgttc   16440
acagatccgt tgcgcgccat gcgttctgga ccgtacggct accttgagca tttcgagcag   16500
ggcagcgggt cggcgtacac ggtcagctcg ggaatgactc tgcggcaagg gcattggaaa   16560
acgcgccctt accaggcgtt caaggtgcag gtgcgcaacg gcggcaacgc cgggacgctt   16620
tactacgatt tcgacctcgg cacgcgcgcc ctgttcgaga ttgaccgcat tatgcacgtc   16680
gaccaggtgt cggcgatcaa gctgcattac gacgagaaca cgcccaagac gttcgacctc   16740
gtgatcggcg acgacgccga gtctgagaat ccgctcgcct caattacccg caccgcgcag   16800
```

```
cacttttgga gtgcgctggc gatgctattc ggatcggggg atttgttctg atgcaactgc   16860
cgaaactcac gccgcgcgag gagatggcgc cgcacgccca ggcgatgcac gacatagccg   16920
acgcgctgca gtacccggcc gacaacatgg ggcgccgcta cgacgttcgg tacctgatcc   16980
cggtgctggc gtttcacctg gcgcgggcgg gctgcgtcat cgaccccgag cgggcgctaa   17040
tcaaaccgcg gcggctgccg ccctcgccgg gcgtcgtcga ggacgcgatc gagtgggtcg   17100
acgtcaacgc ccccaacact atcgacgacg agctggcggg ggcgacgctc gacgacctcg   17160
accggctgtc accggcggcc cgcgctgagc tggtgcgccg cctgggcggc gacggcgcga   17220
aagtggccga ggccgaggca gatacaccgc tcgacgagcg cacgccgtgg cgtgtcgaaa   17280
cgtcgatcca gttcgacgac gaccccgaca gctaacagcc ggcgaatccg ccaatcacac   17340
cgctgacctg cggtggcgct tctgcgtgcc gcaaggtcgg caaacaacga ataggagcga   17400
cctagtcatg gccgaaattc ccgcgaccgg cgacgccgtc aggctgtttc aaacgctgct   17460
gtcggcgacc tggtacggaa tcgtgcgcag caaggacgat cccggcggca tggccgcgac   17520
tatggaaatg atcgacgacg aggcggtcat caccaccgac gtgctgatcg cccgaaggg   17580 tgacaagggc gacaacgccc cgctggtcga cctgcagtgg ccgccgcttg agcaggccgc   17640
cgacctcgaa ccgttgaagg cgagcctcgg cccgaccgac aagggcaagg cgtggtggat   17700
cgggacgctg gtctatgtct ggacgggcag caagttcgag gcggtgcgcc ccggcccggc   17760 cggggccgcca ggggccacac cgctcatcac ggcgtcggcc gaaacgatcc ccatgtcgga   17820
gcgcacgccc gagagcaaag acgaggtgat cccgtcgggc acttctcttg cgccgcacct   17880
gcatttccgg ctgctctcac cgcaaggccc gcgcgggccg tcgacgaaca ttctcgacgc   17940
ccccgactac gacaacacca aggcgcccga ggacgggcag accccggtgt ggtcgtcggt   18000
caagcaaaag tgggtgccgt cgagtttcgc gcacaagcac ccgcggctgt acagcgtgcc   18060
cgaggcggcg tttcagaact tcaccggcgt tgcccagcgg cacccgatcc tgacgtacat   18120
cgtcgaggcg caggattatg cgtggacgcc gtacgtcacc gggcacctca aggcggttgg   18180
catcgagttc gacgtcgacc cgctgacgat cggctgcgag gtgcgcctcg gcgacgcgac   18240
gaccggcgac ctggtcgccc gcgggtttgg caatatcgcg agctggacga acatttcgcc   18300
gcactactcg accagcgccg accggccgc ggcggtggcg cccggcaacg cgtggccgt   18360 cgtgcccgcc ggtcagaccg cgcagatcaa cgtcaacctc tacaacgacg gcatcctcgg   18420
cgcctacctg ttcaaccgga aaggcgcgca actgaccatc ctcaccattc cgacagggga   18480
ataaggctgt ggcataccaa aagtcatacc gcacggtcgt gccgcttgag ccgggcaccg   18540
accgcgacgt ggcgctgtgg cttgtgcgcg agtcgttcga gcgcaaggcc gagggcgacg   18600
ccctggtgct cgtcgagttc gcgcaccgcg acgtcgacgc cgccgatctg ccgccgaagg   18660
ccgagaagca actcggccgc ccgctaaccg atttcgagtt cgtcgagtac accggggtgg   18720
ggcgccgtgc cgaggcagta tgacagcagg cagctcgtcg tcgaccgcga cccgctgcgg   18780
cagctcatac ccgaccccgg caagctgccg aagctcgacc cgaaagtctt ttacgacggg   18840
ttaattcagg gcatcaagat gctgacgggc atcgacctgt cgtcgcccga ggcgctcgtc   18900
gcgagcatca tcgagctgct taaagacgcc gtcggcggcg cgctcgaccc tacgcagctt   18960
ctcgcgacgg tcggcaagat cctcggtttc gtcggcaccc cggcagcat cgacgagctg   19020 gcggcgtggg cctcgacgaa cctgttcgga tggatcgacc ccggccgcct gccgatcatc   19080
ccggtgtcgc atatcgggca gatcatcacg agctgctgc ctaacggcat gttcggaggc   19140
gcgcagtcga tcatcgaccc gaccgggcgg tggctcgtcg acgctgtcga gggcgcggcc   19200
```

```
cgcacggtcg ctaacggcac gttcaccgac ctgctgtcaa cggatctgat cagcgtcgcg   19260
ccgggccagg tgctcaacat cgtcggcaag gtgaagtgga gcggcctgac cgcctcgggc   19320
agcccgatcc agctcggcgt gaccgagtac agcgacgagc gcggcgagaa cctggccggg   19380
cgggctctgg ttgccacgcc tgcgggtcaa accggcacga ccggtggaa ggacgtcgcg    19440 ggcacttaca ccgtcccaca gggcgttaag gccgtgcggg cgcgtgtcag tgtgggcgcc   19500
gaggccaccg cgggcgacgt gtggttcaag ggcgtggatg ccaaccgggg caactcgctg   19560
ctgccgatcg cgctcgtcga gaacctgtcg agtcggctgg cgagcctgct cggcgtcgac   19620
gtgtggcagt cgttccttga cgccgcgaag ggcgcgacgg gcggctcgat cagcgacatt   19680
atcaaccgca ttgtgcacct gggcgtcgac ggctcgttcg acgcctcgca gctcgtgaac   19740
gtgccgaata tcccaatggt gccgggtacg aaggtcggcg gcctcgccgg aaacatgctg   19800
caggactttg gcagtcacat cgacaacatt gtcaatcggc tgtccggcac ccgcgggtcg   19860
aatcaatctc tcgacgacgc cgacgcgcg ctgggcgccc tgcaagacac cgtgctgggc    19920
ctgagccagg acgtgcaaga cctcaagatc gaccaggctg gcacctcgac gtcgggcaag   19980
aggtaccgcg tcgacttcac aacgctgccc tcggggccgt tctccgcggc gccgttcgac   20040
ctcacgtatt ccggtgctgg ctcagggtat ttagagcttg ccggtagggc tcagtggcac   20100
aaggtgaacg acgcgaccg ctctgtgatc gccaggtaca ccgacggcac caacaccgac    20160
accgaaaccg atttccagtt cattcaggcc accgtcggct cgccaccgga cggcgccgcc   20220
gtgaactacg catgcgctcg gatgaacacc gccaagacga cgtttgtcta cgcgatgggc   20280
tttcgggccg ggttttttcgg gctgcagttc cgagccgagc tgggctgcta cgtcaacggc   20340
gtccggtacg tgtttgtggc gaatgcgcct cgacgtaca actacaacct cgccttgaag    20400
gcgggcgtgg gcggtaaccc gtaccgtttt caggtgctct cgggcacgac cgtggttatc   20460
gactacaccg acaccagccg cgttagtcag atcggcgcgg cgttccgcgg gtggggtttc   20520
cgctccgaca ccggcaacag cggtagcgat gcgcctgccc ctgcggtgtt cgtcggctgc   20580
gccgataacg ccccggtggg cgtgcagggc accacatttc gggcctatcg ttcgctgtcg   20640
agttctgtgt cgaaaccggc gggcaatgtg ccgctcccgg cgaacacgtt cgacaccgtc   20700
gactacatca gctcggactt gaagtggaat cccaccacta acgagataac ggttctcaag   20760
gccggtacct acctgtgctc gatgcgcctg caaggcgcgt cggccctcgg ctttggtaac   20820
ggcaagcggg tttacccgtt ctggttcgtg ggtggcgcag cgaaggcgat gggccacgac   20880
aaatatgcct tgaacctcaa cggtttcggt gccccggcgg cgtcattgga ggatgcgatc   20940
ggcggcgacc cgttcgtcta ttacgttccc gagggcggcg tcatccgggc aggggcgggc   21000
aacgccgcga atgccgcgat agctctcgtc ggcgacagcg ccgggctgtc aacatggctg   21060
accgtcgcca gggtgggcta atgccccgac ggctcaacgt atctcagcac atcactactc   21120
actaggagcg cgtaaatatg gcagacgtcg aaaacacggc cgacatggtt caggcggtca   21180
agcagcggct cggcgaggag ctttccgagg agcaggtgca cgccgtgctg ccgcgtgga    21240 acagcgtgcg ggcgcagggc gatccggtcg gcatggtgcg ccgcgacgag gagtcgggca   21300
aggtggcgca ccgcgtcgtc gtcgaggccg tcgagcagtg gcgcgtgagc ggggctgacg   21360
gcgaccagta caacgacctg cagccgacgc tgccctggcc ggtgctgttc gacccgcgct   21420
aatgccttgg acgccaacgc ccccggcggc cggcgcagc agctacggct ggtcaactaa    21480
cccggccccg ctggcgcagc ccgcgccggt cgggccgggc tggttcgtgt cgctgcacga   21540
```

```
gccggccgct gcgctgagta tcagcaccgg cgacgcccgc gtcgtcgtgc agaccgtggc   21600
ccaggcgcgc ggcatcagcg aggccgacgc ggcgctgctg gtgcacatga tcgggcaggc   21660
gtcgagcgtc agctcgtcga ccgcggcggc ggccgagcac gtgttcgccg acgccctggc   21720
cgcctcggcg agcgcggccc gcgccgacct ggtcgtggaa atcgtcgccg aggcgctcgg   21780
cgtcagcgcc accgacgcgc tgttcgcgct caagttgacc gcggcggcca gctcggcgag   21840
cgacgccgtg gcgaccaacg ctttccggc gatggcccg ctaccgcaac agttcacggc   21900
cgcgggcaac tacacgtacg cgatcccgta ctggtgccgc ttcatcgaca ttgtggtgct   21960
cggcggcggg ggcggcgggc aggcgtctgc ggcgctgttc aactacggtg cgcccggtga   22020
tcccggccag tatcaggccg tgacgctaga gcgcggcgtc gacattccgt gggcggtggc   22080
ggcgatcacc ggcaccgttg gcgacggcgg tagcgcgtgg ggcacgtacg gcgccatccc   22140
cggcggccct ggcggcaata cgacggcgac gttcactggc ggcggcacgc tcagcggccc   22200 aggcggggc ggcggtatcg ggtgggccac ccaagcgggc tctcgcggcc ccggccccgg   22260
caatttcacc tataacgggc agctctacgt cggcggtgga ctggcagacc agggcgccaa   22320
caaacccggc aagccgcctg gtggcgccgg atcaggtaac tctcccggcg ccggtggggc   22380
tggcccaggc gcacccggcg cagtgtggtt ccgcgcctat cagtgaggag tgcaacgaaa   22440
ttgaatcctg acgacgacta cacgttcgcg ctccggtacg agtggctgcc cgaccccggc   22500
gccgaccccg acgacccggc caactggcgc gaatggatca tgcccgccgc gaccctggcc   22560
caggccgagg gctggctcga cgcggtggcg caggcagata cccgcacgc ccgcgggttc   22620 gccatcgtct actcgcccaa ggtcacttgg cggccctggc cgcccgccga cgactgagcg   22680
catgctcgct ggccctgata acggccgagc gggtttcgta gcacgtgcgc ctcgcccgta   22740
gctaaccgcc ggcaaaaact cgagcacccc ctctcacctg cggataccte gcgaaacggc   22800 gcgaggtcgg caaacactgg ataggagcac cgtggcagca acggacgcat tcaagctcgc   22860
gatcgccaac gcgatcggcg cgcaaggcgc actgatcagc ctgcactcgg ctgaccccgg   22920
caagaccgac gcgacggcca acgcgaccga aattagcggc gccggataca cgcgcaagct   22980
gaccgcgtgg ggcgccccgg tcatcgtgtc gggcggcgcc gacgacggca aggcccgcat   23040
caccggctcg acgcagcagt tcaacgtgcc cggcggcgtg ccgatcacgc actacgccgt   23100
gcgcaaggcc gacagcacat tcctgtacgg caagccgctg gcgcccggcg cgaccctcac   23160
cggcaacggt gtcatcgacg tcacgccgac acatacctac gacctgacct agctcgaaat   23220
ggtcggcgtc gagggcattt tcgcagcatt gtctgcggct gtggtgctcg gcgccctcgg   23280
gcactggctc tatgacgtgc tggcgcaccg gcgctacgac aacgacgagg gatacgacac   23340
atgagtttca cccggttcct gcaggatgac ccgctgctca cccgcgagca agtgatggcc   23400
gagctgattc gggtcgccga cgagctgaac atgcccgaca agcgcggcgc ctgcgtcatt   23460
gcgggcatga cgatttcgca agaggtcggc gtaaaggaca acgacccgcc gttcgagcgg   23520
cggttctggt gcccggccaa ccgcgccgac cccgaatcgt tcaactaccc gcacgactcg   23580
gaatcgaacg acggccgctc ggtcggctac ttccagcagc agaaggggcc taacggcgag   23640
ctgtggtggg gcacaacggc atccgagatg aacctgcaca gcgccgcgac gcagtttatg   23700
acgcggctca aggcggccgg atacaacgcg agcaacgccc aggcggcgaa cgactcggcg   23760
caggcgatcc agcggtcggg cgtcccgcag gcgtacaagc aatggtggga cgacattaac   23820
cgcctgtaca acaaggtgaa gggctcgggc ggtggcccgg cgcccgcgcc taagccgccg   23880
cagtcggggc cgtggaccgg cgacccggtg tggctggccg acgtgctgcg cgccgagggg   23940
```

```
ctgaacgtcg tcgagctgcc cggctggctc gaccgcgggc acggcgacat gggccgcttg    24000
tggggcgtgg tgtgccatca caccggcagc gataacaccc cgtcgagcga gattgcgttt    24060
cacccgtcgc tcggcctgtg ctcgcagatt cacctggcgc gcaacggaac tgtgacgctg    24120
tgcggtgtcg gcatcgcctg gcatgcgggc gtcggcagct atcccggcct gcccgaggac    24180
aacgccaacg cggtcactat cggcatcgag gcccaaaaca gcggcaccta tgacggcgca    24240
ccgcaccgga cgaattggcc tgacgcgcaa tacgacgcct atgtgaagtg ctgcgccgcg    24300
atctgccgcc gcctcggcgt gcgcgccgat cacgtgatca gtcacaagga atgggccggg    24360
cgcaagcaag gcaaatggga tccaggcgcc atcgacatga acatctttcg cgccgacgta    24420
cagcggcgca tcgacgccca tcaaccaaac ggagaggacg atttcatggc cgcactatca    24480
gccgacgagc agcgcgaggt gctgaacctg ctgcgcgtcc tggccgaccg gcggttcgtc    24540
agccgcagcc cgttccgcca ccttggcgag gggccgagcg aaactgtcgc cgggttcggg    24600
ctcaacaccg acgccctcaa tcacgcgcag tacacgattg agcttgcgcg cctgggcgac    24660
ccgacgcacc tcgccctgct gcgcgaggtc gccagcgccg agggtgactc gcgctatccc    24720
gaccggcagt acgacgccaa gctcgccaag cgcgtgctcg ccgaaatcga gggcgccgca    24780
acggcaccgg ccaagccgag cacgccgagc gccccgaccg agcccgcccc cgaggcgccc    24840
acgccgccgg tcaaggccgc gtgtgcgctg tctgcggccg ggtgcgtggt ggctggctcg    24900
acctcgggcg gtggctgcgc cctgtccacc gacggcaccg gcaagtgcgt tgtgaccgcc    24960
gcgaccgacg gcggggccgc ctgatggcct gggtcggttg gcagctcggc atgcagggg    25020 agcaggtcaa ggtgatacag caaaagctga tcgccaagta ccagtgggtg cgtgaccgtt    25080
acccgcggct gacggccagc ggcgtctatg acgtgaacac gcaggccgcg atcgtcgagt    25140
ttcagttccg cgcagggctt cccgtcaccg gcatagctga ctatgcgacg caggttcggc    25200
tcggcgcggt ggccccggcg ccgccgccgc ggcagcgcat catggtgctg acgtttagcg    25260
gcacctcggc cgacatgtgg accggctatc cggccgacgt cgcgcgtgcg ctcgacccgt    25320
cgatcttcta ctggcagcca gtgtgctacg gccccaacgg catcccgcg atattcccga    25380 tgggttccag cgccaagagc ggcgaggtcg aggggctgcg gctgctcgac gagaaggcgc    25440
gcgatttcga ctacatcgtg cttatcggat actcgcaggg cgcgctgccc gcgtcgcggc    25500
tcatgcggcg catcctgtcg ggcgacctgc agcggttcaa gtccaagctg atcgccggtg    25560
tcacgttcgg caacccgatg cgcgagaagg ggcacacgtt ccccggcggc gccgaccccg    25620
gcgggcacgg cctcgacccg cagtgcctcg tgaatacgcc cgactggtgg cacgactacg    25680
ccgccaaggg cgacatttac accgtcggct cgggcagtaa cgacgagaag gccaacgccg    25740
acatgacgtt catttaccag ctcgtgcagg gcgacattct cggcatgatg ttcggcaccg    25800
gcaacccgct cgacattctc ggcctgctcg gcggcctcgg tggcggcctg ctcggcggcc    25860
tgggcggtgg cctgctcggt ggcggcaagg gtggcctgca gttgccgagc ggcctggtgc    25920
tccccggcgt ccagggcggc gcgctcaccg accaccagcg cggcctcgtc gaggcggtgc    25980
tggcgctgct cgctaacccg ttcgccgagg ttcggcggc ggtcaaggcg attgtgtccg    26040
gtgtcgggtt catcgccacc aacccgccga cggcgccgca catcgagtac cacattcgcg    26100
aggctgcgcc cggcgtgacg tatttccagc acgcgatcga ctacctgcgc caggtcggcg    26160
cgtccgtcgc cgctcgcgcg gcctgacccc gaggagtcaa cccccgatga tgtcgatttt    26220
ggatctgcgc tcgcgcgacg acgtgcggcg cttcattcac agcgtcgccc cggcgatcgc    26280
```

```
cgtgctgatg gtcagcatgg gcgtgctcga ccgcaacgtc gcaatgctcg gcgtggctgt    26340
cgtgctggct gtgttcaacg acaccctggc tcatatcaac tcgtccgatg cgttccgcaa    26400
gtggttctat ccggtgctga cgtcggctac cgcaatgctg atcgggctgg gcatggtgac    26460
cgacgagcag ctcacgccgt ggatcgcgat tatcaccatt ctgatcggcg cggtgttgc     26520 ggctaagaat gcgctgcccg aggagtgcga ggccgacgac gacgagccgt caggcaagca    26580
cgcgacgaca tgacgccctt gcgggcggtg ccgggcatgc tggctcgtgc tgacaacgcc    26640
tcggcggcga agctggacgg catgcggggg atgccatgac gtaccgctac gtcgagaacc    26700
gggtgctgcg tttcgtgcag ctcgcgctgc tcgtcgacgc cgtcgtgcgc ggcgcgagct    26760
ggatcgcgac cccggcgagc ggcataccc cagcgatcgg cctggccgcc gaaggcaccg     26820
cagccatgtg ggtgtgggc gccgtattcg ccgtgtttgg catcttgggc ctgctcggcg     26880
agctgtggat gcacctcggc gagtctgagc atcgcgcgtg gccgtcattc ctggcgtacg    26940
ccgcgctgct gttcctgttc gccgggctgg ccctgtcggc ggtcaataac gtcatcacaa    27000
cgcacgcaac ggacgggttc agcgccccat acactttcgc ccttctcgcg ttgctgcatt    27060
gggtgttcgc gaggcggcgg aagcatgtcg gctgagctga tcgagaagct gccgcagcag    27120
tgggtcggca tcgtcgtcct ggtgctgttc gtcgtctacg tggccgggca gctcatcgag    27180
aaatccgagc gcgtcgcgaa gctgctgccc ctcggcgtgt ggtggcgcga gcgcaaccgg    27240
cgcaagtctg cggtcgaccc ggccgagctg acacgcgcgg tcgaggcggc ccggcatgcc    27300
tggtcgcgcg aggagaacgc cgcactggcg gcccttgaga ccgcgtcgc cgtgatcgcc     27360 gcgatttcgg agcaccaggc cctcaacatc aaagagctgc aagactcggt gcgggcgttc    27420
acggcgttct ctgtgtacga cgcgcgctgg caccaccgcg ccgacgtcgc cctggctgac    27480
tgcccgatgt gcgacctgcc cgaccacctc gattacttcg ctttcgagcg gctgtggcgc    27540
gaagatccgg ccgccgccgc gaggttgcct gtatgagcct cgctgaccgc ctcgggccgc    27600
tgacacgagc cccgatcggc tgcgcggtgt ccgctggta cgagggcctc gacgacaccg     27660
accggctggc gttcgactcg tgggtcaacg gcggcggcag tatctcgcag ctctggcgcg    27720
agtgctgcgc cgaccccgac aggccgctgc atatcagccg cccccggttt tccgagtgca    27780
tcaaccaaca ccaccgcgga ggccctcgtg tcgctagctg accggctgag caccccggcg    27840
gtgcccgacg agaagtaccg cccgtcggtc gagttcgaca ccgcgcggcgc cacgatcgac    27900 accggcgcgg tcgagcagga gcccggccag ccgcccgagt acgccgagct gctgcgccag    27960
gtcggccgcg accccgagcg gttccggctc gtggcgatcg accgcgagaa gcactggcag    28020
gtgccttacc gcccgatcga gggcaccgac gagcgcggca agccgatcct cggcgagctg    28080
acgaccaagt ggctcgcctc gtactcgctg cgcgtcgaac ctatcgacca gggcggcaac    28140
gaccttgagg cgctgatcgc cgaggcccgc aagcgcccca cgatcgagcc cggccagctc    28200
ggctcgccgt attggttcgt cttcaggc ggcgacctgc agctcggcaa gcgcagccgc       28260
gacggctcga ccgagcagat cgtcgagcgg ttcgtacagt cggtcgaggc cgccaaggct    28320
caactgcacg cctgggcacc cctcggtatc gcgggcgtgc agatcagcct gccgggcgac    28380
tgtttggaag gcgtcgtgtc gcagggcggg cgcaactcgt ggctgacgca ggaaacgatc    28440
gccgagcaga cccggctgct gcggcggctc atggtgtaca cgatcgacga gctggcggcg    28500
gcccccgagg tcaagctcga cgtcgtcggc ggcaaccacg acgacgctaa ccggcagtgg    28560
aacaccaagc ccgcgacaa ttgggcgacc gaggcggcga tcgccgtcga cgacgccctc     28620
aagctcaaca ccgccgcgta cgggcacgtc gaggtgcgca tccctgagtc atggtcggga    28680
```

```
cacatgaccg tgccggtcgg cgacaccgtc gtgaccgtga ttcacggcca ccagtggcgc   28740
aaagggcagg ccctcaagtg gtggagcgag caggcggtgc acaaccagcc gcccggcgct   28800
gcgcacgtgc tgcagcatgg gcactggcac accgcggcgt gggaagcgca cgccaccaag   28860
acgatcgtgt gctcgccgac gttcgactgc gggtcggact ggtaccgcga gcggcacggc   28920
gccgagtccc ggcgcggcgc cctcacgtat ctgctgcgcg cggcgaggt ttcacgcctg    28980 agtgtcgtgt agctaaccgc cggcaaaaac tcgagcgcac ccgctaagct gcagcaatgc   29040
gctgcgcccg tccgaagtca gcaaacagcg cccctcggct cacgccgggg ggcgtttcgg   29100
cgtttctagg gcctgttgac gcgccaacag ttctgcgcct aagctgttgg ggtatcaaca   29160
ccccagcgga taggagcccg acatgacaac ggcattcgcc gacccgacga tcgaggacgg   29220
tatcgacatg gcccgaggca gcaggtgcg catcgacggc aaggtgcgca cgatcccggc    29280
cgacaaggtc gagcagtacg aggcgatggc aacccgcatc gacgccctgt ccccggcga    29340 ccgcgggcac gagcgccagg ccgcgctgaa agccgccgcg cgcttcatcc tcggcgacct   29400
gaccgtcagc ggcgccggtg acgacctcga tctcgcccgc cgggcgcagg aggaggccgc   29460
cgcagcggcc cgcgcggtcg ctatcctcgc gatcgagaac ggcgcagcg agcagggcac    29520 ggcccgcgag atgggcgtcg accggctgac cgtgcgcaag tggaacggca aggtcgaccg   29580
ggcatgagcg acgaggtgtg ggtgctcgac ttcgaggccg aggggccgga ccgggcgac    29640 tatgtcgggt atcagtcggt gcaccgcacg cgcgacggcg cgagtaaccg gctgctcgaa   29700
cgcctcgccg acgtcgacgt cgacgtggcc gaggtcgagg cgctcggcgg cgcccaggcc   29760
gacgacggca gctacgcggg cgagctggac gccgacggca tgacgatcag ctacggcgtg   29820
caccgcatgc cgatcgagga ctagcgtcac ccgcccggcc cgtagcaatc tgctacacga   29880
ggcgcccctg tcgattcgtc ggcgagggcg cttcgtgtt gacgggtcaa cagcccgcgg    29940
tgtactgttg aggcatcaac agcactacgg gataggagcc caaaatgacc acagcgacat   30000
ggactaaggc cgaggccaag gcgagcgacc gcgagtacgc ccgactggtc ggtatcgccc   30060
aggccgccag cgccgccgtc gacaccgccc acgagcgcgc cctgacggcc gccggggcga   30120
gcatgcagta cctcaacggc gggtaccgcc gcaagggcct gagcttcgac cgtggccgca   30180
ccgaggccac cctcgaccag gcccgcgcga tcgcctcggg caaggagcag tcgccgagcc   30240
ggtacgccga cgtcgagcgc gccgccgagg ccgtcgcccg gtacgacgcc gcggtcgtcg   30300
agtaccgcga ggccaacgcc gcggcccgcg cctgggacga cgcgcattac cagggctggc   30360
ggcgcttttt cctggtgccc ggcggccaca ttcacgagtc gaccgcctgc agctcgctgc   30420
gcatcacgac catgatcgtg tggctgcccg agctgtcggg tgaaaccgag gccgaggcgg   30480
tggccgagca cggcgccctg ctgtgcacca agtgcttccc gtcggcgccg gtcgagtgga   30540
ccgtcggcaa cgtcgacccc gacaagtgca acgggcgccc cgacatggac cgccgccgcg   30600
gccggtacgc gccgtgccgc gagtgcgggt acgtcggcca catcacgacg cacggcaacc   30660
tgcgcaagca caagcgcgag agcgcctgag agccaacgag aaacgcccc gacccggtcg    30720 caccggcggg ggcgttttcg tgcgcctgcg gggcgctcag ccgggcaggt gacccggctc   30780
gtcgggcagc accgtgtcgg gcgtgaccgt gtactgctcg cggtcgttga tcttcatgtc   30840
gacgaaataa ccgccgtacg tggtgcacga gacatagctg cgcccatagc agctcgtgcg   30900
cgtcggcacc tggtgcgccg gtgtccacac gctgcgcttg cgctcccagc tcccgtcggg   30960
ctgcaccggg ccgtcgcaga tcgtgcgccg ctggctgccc aggaatcccc acagcaccgt   31020
```

-continued

| | | | | |
|---|---|---|---|---|
| gtcgcagttg | gggccgaggt | caggatcggg | ccgagcgtgc | gccggggcgg cggccagcac | 31080 |
| ggcaccggcg | ccgatggcac | cggcgacggc | gagtgttgcg | gctgttttga atccgatcac | 31140 |
| gacgcacccc | cgagcgccag | gtgggcgccg | cccgagaaca | tcgagtcgtg caggatcagc | 31200 |
| tcggttgcct | cggtgccggg | cggcacgtcg | aacgcgacgc | gcgcctgaat cgcgttgcct | 31260 |
| gggttaatgt | ctccggtcct | gcaggtagta | ccgcgatttt | gacatttgca gcgcctctaa | 31320 |
| tatctcgcgc | agcttgagcg | gtctacccac | taagtagcca | agcactgcgg caaggctctt | 31380 |
| ggcggtgtcg | tcgtctggca | cctgggtgtc | ctgtctatta | ggggcgggtc cgaaatcgcc | 31440 |
| cgtatggcgt | gtcactttag | tctaggtttc | tggactaaac | aataggcttg agcagcgatt | 31500 |
| atgagaaacg | ctaatcgttc | gcgcgtgcaa | taagtcgcgc | ccaatggtgc agattctgga | 31560 |
| caagtgggct | atggtgacag | ccatgacagc | cccgcgacac | gagctgcgat ggaatcccgg | 31620 |
| caaagtctca | aaaacactgg | cccgcctcgg | tattcgtgac | cgcaccgccc tggctaagcg | 31680 |
| cgtcagcatg | cccaagagca | cgatatacgc | ggcgttcgac | gccgactggt caggcgtagc | 31740 |
| aacgaccaac | gtgttagcgc | aggtcgcagg | cgagttaggg | gtgtccctgc tcgacctggt | 31800 |
| cgccgagccc | gcaccgcgcc | gaaaccagaa | agtgcagaaa | actgcaccgc gccggtcggt | 31860 |
| gcagaaaact | gagcaattcg | gcgcgacggt | gctgctatga | ccggcgcctt gctgacctat | 31920 |
| cccgtcgccg | acgtcgcgcg | acgtatcccc | tgctccgagc | ggtggctcac cgagcagatc | 31980 |
| cgcgccggtc | gcatccccgg | ccgcaaggtc | ggtcgtcact | ggcggatgac tgaggccgac | 32040 |
| atagaggccg | ctctcgaatc | gttccgcgtc | gcccccgagt | cgggtcgcaa gtctgtcgcc | 32100 |
| gccgagcgcc | cgttcgcgct | caccgccacc | tcgcaacgcc | ggattagggg ctgacgcaat | 32160 |
| gcaactcatg | cgccacatcg | aggagtgccg | ccgcctgcag | gcacagattg acgagctgac | 32220 |
| cgccgagctg | cgcgtcgtca | ccgacgagcg | cgacgccgcg | ctgcgcgagc gcgacgagct | 32280 |
| ggccgaccgc | ctggccgtcg | ccgaggccga | caaggcgtgg | gggcgcgagg agcaccggcg | 32340 |
| gctgcacaac | ccgatgcccg | acatggaccg | ctgcggctga | tcgccgccta acgacacaa | 32400 |
| cccccgcacg | aggcggggc | tggccgacac | aaccaaggga | taggagccac ttgttatgcc | 32460 |
| gacacagagt | ttagcgccag | atcggcccgc | agtgcctagc | gccatgcggg cgtttgcgtc | 32520 |
| gaccccggcg | ccgtggtgcg | acgactgccg | ctgcgtgcac | gcccggccgt gcgaggcgca | 32580 |
| gcagcgcatc | aaccgcgccc | tcgacgccct | cgggttcgcg | ctgctcatcc tgacgtcgat | 32640 |
| cctgctcggg | ctcgccgcgg | gggcgctgac | cctatgagcc | tcaaggacat aacgctcacg | 32700 |
| cacgccgagc | tgaacctcgc | cgcgcacgtc | gtcgacaccc | acatgacaca gggcttcacg | 32760 |
| gcgcacggcg | cggtggcctc | ggcgattcgg | gctgtcaact | cgatgcgcaa ccacccggcc | 32820 |
| gcgtaccgcc | gggtcgacct | ggcgcagctc | aagcaatctc | agcgcagccc gcaccgcggg | 32880 |
| gcggggcggt | tccgcgtcgc | cgactgcgcc | gactgccagc | tcgacgacaa cacctgcccc | 32940 |
| ggccaccgga | tttaggagct | atcaccgcat | gtctgaccta | gtgattttcg acagctgca | 33000 |
| gcaaggcgag | gagccgcgcg | actacgtgcc | cgcgttcgag | cgggccgtgc tgtacgccat | 33060 |
| gcagttcaaa | ccgatgtacg | agggcaccgt | gccgcaccgg | gtgcgcgcca agcgccgcga | 33120 |
| gcgtaaccgc | gtcgcccgcc | gttctcgcaa | gatcaaccgg | aaagccatct agcgcaatga | 33180 |
| cttacgaccc | aactaaccgc | gagcaagaat | ccaaggatcg | ccgccgcatg cggatcgcgc | 33240 |
| agcgcaagcg | cgaggcccgc | tcggcgatgg | ccgtcaagac | gtacgtgctc gacgacgtcc | 33300 |
| tgcccggcct | gccgccgatc | cccgacaccg | acgacgtgtg | caaggccctt ggcatcaagg | 33360 |
| cccgcacgac | gctgcacaac | gtgctttacc | gtcaccgtga | cgaaatgatc gcgggcggat | 33420 |

```
gggacgccgc cgcaggcaca ttcacgcgcg aggccgttgt gcggctgtgc ctgctgctgc    33480
gcgccaccac ctcgcgcaag gcggccgaag tcgccgaggc ggtcggcgcc cgcgatcgcg    33540
tgatcaagtt caacgccagc aaggtgccgc acattcggcg ctgccaggcg ttgatagaca    33600
aggcattcgg ccttgctgag cgcgtgcgcg acgaagatcc cgccgaggtg tggcacgacc    33660
tcaatcagat ggacgcctac acgctgcagg gcatcaccgt ggccctggcg gcgatggtcg    33720
acctcgactc ggcgaccggc ggtgtgacgc agtggcttag ctcgctggcc ccgtctaagc    33780
ggcaccccgg caagggcaac ggcggcgccg cgagcggttt ggcccggctg gtgccgacac    33840
ccgatgaggc gcagggcatc ccgctgggca agatcctgat caggcgcctt aattaagatc    33900
cctatagtga gtcgtattat gcggccgcga attctcatgt ttgaccgctt atcatcgata    33960
agctctgctt tttgttgact tccattgttc attccacgga caaaaacaga gaaggaaac     34020 gacagaggcc aaaaagctcg ctttcagcac ctgtcgtttc ctttcttttc agagggtatt    34080
ttaaataaaa acattaagtt atgacgaaga gaacggaaaa cgccttaaac cggaaaattt    34140
tcataaatag cgaaaacccg cgaggtcgcc gccccgtaac aaggcggatc gccggaaagg    34200
acccgcaaat gataataatt atcaattgca tactatcgac ggcactgctg ccagataaca    34260
ccaccgggga acattccat catgatggcc gtgcggacat aggaagccag ttcatccatc     34320
gctttcttgt ctgctgccat ttgctttgtg acatccagcg ccgcacattc agcagcgttt    34380
ttcagcgcgt tttcgatcaa cgtttcaatg ttggtatcaa caccaggtttt aactttgaac   34440 ttatcggcac tgacggttac cttgttctgc gctggctcat cacgcaggat accaaggctg    34500
atgttgtaga tattggtcac cggctgaggg ttttcgattg ccgctgcgtg gatagcacca    34560
tttgcgatca ggcngtcctt gatgaatgac actccattgc gaataagttc gaaggagacg    34620
gtgtcacgaa tgcgctggtc cagctcggtc gattgccttt tgtgcagcag aggtatcaat    34680
ctcaacgcca aggctcatcg aagcgcaata ttgctgctca ccaaaacgcg tattgaccag    34740
gtgttcaacg gcaaatttct gcccttctga tgtcagaaag gcaaagtgat tttctttctg    34800
gtattcagtt gctgtgtgtc ggtttcagca aaaccaagct cgcgcaattc ggctgtgcag    34860
atttagaagg cagatcacca gacagcaacg gccaacggaa aacagcgcat acagaacatc    34920
cgtcgccgcg ccgacaacgt gataattttt atgacccatg atttatttcc ttttagacgt    34980
gagcctgtcg cacagcaaag ccgccgaaag ttcctcgacc gatgcccttg agagccttca    35040
acccagtcag ctccttccgg tgggcgcggg gcatgactat cgtcgccgca cttatgactg    35100
tcttctttat catgcaactc gtaggacagg tgccggcagc gctctgggtc attttcggcg    35160 aggaccccttt cgctggagc gcgacgatga tcggcctgtc gcttgcggta ttcggaatct    35220
tccacgccct cgctcaagcc ttcgtcactg gtcccgccac caaacgtttc ggcgagaagc    35280
aggccattat cgccggcatg gcggccgacg cgctgggcta cgtcttgctg gcgttcggtg    35340
gctttgttga ataaatcgaa cttttgctga gttgaaggat cagatcacgc atcttcccga    35400
caacgcagac cgttccgtgg caaagcaaaa gttcaaaatc accaactggt ccacctacaa    35460
caaagctctc atcaaccgtg gctccctcac tttctggctg gatgatgggg cgattcaggc    35520
ctggtatgag tcagcaacac cttcttcacg aggcagacct cagcgctagc ggagtgtata    35580
ctggcttact atgttggcac tgatgagggt gtcagtgaag tgcttcatgt ggcaggagaa    35640
aaaaggctgc accggtgcgt cagcagaata tgtgatacag gatatattcc gcttcctcgc    35700
tcactgactc gctacgctcg gtcgttcgac tgcggcgagc ggaaatggct tacgaacggg    35760
```

```
gcggagattt cctggaagat gccaggaaga tacttaacag ggaagtgaga gggccgcggc    35820
aaagccgttt ttccataggc tccgcccccc tgacaagcat cacgaaatct gacgctcaaa    35880
tcagtggtgg cgaaacccga caggactata aagataccag gcgtttcccc ctggcggctc    35940
cctcgtgcgc tctcctgttc ctgcctttcg gtttaccggt gtcattccgc tgttatggcc    36000
gcgtttgtct cattccacgc ctgacactca gttccgggta ggcagttcgc tccaagctgg    36060
actgtatgca cgaaccccc gttcagtccg accgctgcgc cttatccggt aactatcgtc    36120
ttgagtccaa cccggaaaga catgcaaaag caccactggc agcagccact ggtaattgat    36180
ttagaggagt tagtcttgaa gtcatgcgcc ggttaaggct aaactgaaag gacaagtttt    36240
ggtgactgcg ctcctccaag ccagttacct cggttcaaag agttggtagc tcagagaacc    36300
ttcgaaaaac cgccctgcaa ggcggttttt tcgttttcag agcaagagat tacgcgcaga    36360
ccaaaacgat ctcaagaaga tcatcttatt aaggggtctg acgctcagtg gaacgaaaac    36420
tcacgttaag ggattttggt catgagatta tcaaaaagga tcttcaccta gatccttta    36480 aattaaaaat gaagttttaa atcaatctaa agtatatatg agtaaacttg gtctgacagt    36540
taccaatgct taatcagtga ggcacctatc tcagcgatct gtctatttcg ttcatccata    36600
gttgcctgac tccccgtcgt gtagataact acgatacggg agggcttacc atctggcccc    36660
agtgctgcaa tgataccgcg agacccacgc tcaccggctc cagatttatc agcaataaac    36720
cagccagccg gaagggccga gcgcagaagt ggtcctgcaa cttatccgc ctccatccag    36780 tctattaatt gttgccggga agctagagta agtagttcgc cagttaatag tttgcgcaac    36840
gttgttgcca ttgctgcagg catcgtggtg tcacgctcgt cgtttggtat ggcttcattc    36900
agctccggtt cccaacgatc aaggcgagtt acatgatccc ccatgttgtg caaaaagcg    36960 gttagctcct tcggtcctcc gatcgttgtc agaagtaagt tggccgcagt gttatcactc    37020
atggttatgg cagcactgca taattctctt actgtcatgc catccgtaag atgcttttct    37080
gtgactggtg agtactcaac caagtcattc tgagaatagt gtatgcggcg accgagttgc    37140
tcttgcccgg cgtcaacacg ggataatacc gcgccacata gcagaacttt aaaagtgctc    37200
atcattggaa aacgttcttc ggggcgaaaa ctctcaagga tcttaccgct gttgagatcc    37260
agttcgatgt aacccactcg tgcacccaac tgatcttcag catcttttac tttcaccagc    37320
gtttctgggt gagcaaaaac aggaaggcaa aatgccgcaa aaaagggaat aagggcgaca    37380
cggaaatgtt gaatactcat actcttcctt tttcaatatt attgaagcat ttatcagggt    37440
tattgtctca tgagcggata catatttgaa tgtatttaga aaataaaca aataggggtt    37500 ccgcgcacat ttccccgaaa agtgccacct gacgtctaag aaaccattat tatcatgaca    37560
ttaacctata aaaataggcg tatcacgagg ccctttcgtc ttcaagaatt cgcggccgca    37620
attaaccctc actaaaggat cttaattaag gatcgcgaag gcgacgcagc gcgtgcagca    37680
gcggcagatc gggctgctga cgacgcagcg cgagattatc gacgaccagc tcgccgacgc    37740
ggtgcgcaag cgcaacgagg ccagcggcct gattgcgcag gctttgggca tgttgaacgc    37800
tcaacagtga gcactcggca tgaccgttat cgctgaatac atctaggcgc atagacatag    37860
cagcgtgcct caccacaact gccccggcga cgactgcgt cgttgcgagg cgcgcattgc    37920
ggcgatcgag tacgagcgcg aggtcgcgca cgacgattac ccgcagttct acgacggcac    37980
ctagagcccc gcgggcgctc gcgcgggaat ccacaacggg cgcaaatgat cacgaaggaa    38040
acacaggaac acatgagcaa cgattcgtac ggattcctcg caggcggcgg cccggcgtcg    38100
ggcaagttca aggcccacgg cgacaccgtc ggcggcccga tcgtcgtcga gccctcgcag    38160
```

```
cagcagcaga ccaacatgga caacaagccg ctgacctggg acgacggcag ccccgcatg   38220 cagctcgtcg tgaccgtgca gaccgatctg cgcgacccct cgatcgagga cgacgacggc   38280
aagcgccgcc tgttcgtcaa gggcgaaatg cggaaagccg tgcagcaggc cgtgatcgcg   38340 gccgggggcca agggcctcga cgtcggcggc gagctgcacg tgacctacgt cggcgacggc   38400
gaaccggccc ggcccggcct gacagcgccg aagctgtaca gcgccaagta catcaagccg   38460
agcgccgctg cgctggcgac cgccggtggc ccggcaccga gcagcgacct gcccgagggc   38520
gtgacccccg aggcgttcga ggcgctgcag aagctcggca tggtcaagta gcacaccgca   38580
tttcgaggcg ggccggtggc gtggttttgg gaccgtcacc ggcccgtttc atcaccaggg   38640
ataggagccc cgagaacatg atcaccgttt acacgaccgg acctgagtgc cacaagtgca   38700
acctgaccaa gcgcgccctc gacaaggcgg gcgtcgagta caccgagtg cgcctcgacc   38760 aagatcccgc gctcgcagcc gatttcaagg ccaaagggca aagacggcg ccgatcgtgc   38820 gcgacgcgct caccgacaca atgtggtcgg atttccgcgg cgacctaatc aaggccgcga   38880
tcgcggctcg ggcggtggcc tgatggacgg cgagctggtc gccaaggtgc gcgacgcgat   38940
cgaggccgag ctgaaagcgc aagcatggtg cctgatcggc gtcgacgcc gggtcgactg   39000 cgtcgacggc gacattgaca cccacgcgat cgccgaggcc gctgtcgacg cgatcgaggg   39060
gcgatcgtga ccgcgagct gctggcgctg cacgaccgga tcaagtggca gcgcgccgac   39120
ggccgctgcg agtgtcaggg cgagtgcggc cggtcgcacc gtttcggcgg cgtgcactac   39180
cgctgcccga ataagcacgg caactccgcg gtgcatggcg cgacaaggt cgtgacgctg   39240 accgtgcgcc ccctcgacgg cgacgagcga aacctcgacg agcgcaacct catcgccatg   39300
tgccaggcgt gcgtgaagcg ccaccgcgcg aaatgcaagg ccgacgccga gcgtgaggcc   39360
gagcgccggg cgaccgaggc gcagcacgag tcgctgttcg agctacccga ggtcaccggc   39420
gcggccctga cgccgccctg actgcccccg ccccaatgtc gcaccaggcc caacccgata   39480
gggacagaat gaatttcacg gagctgctcg actcgctcgg ctacatggag ggcgagcacc   39540
tgtcgctctg ccaccaggtg cccggccaca acttcatggc gaacgtgatc gagttcgacg   39600
accgcgccca agctaaggcg ctgcggtacg tcgacgactg cgacctgtgg ttcggcgtca   39660
acccgacccg gcgtcgcggc gccgacgaag gcggccgggg cacggccgag gacgtcaccc   39720
ggctggccgc ggtgtggtgc gacctcgacg tcaagccggg cgcgtgccgc gacctggcgc   39780
acgcctggca gatcatcgac gagctgagca tcctggtcgg ccagcggccg acggcggtcg   39840
tgatgagcgg gcacggcctg cagccgtatt gggagattga ggacggccag ctcgtgccgt   39900
gtgccgccga cgccgacgac ccgacgatgc aggccgccag cgaggagctg cgcgcggagg   39960
ccgccgcggt gctcaagcgg tgggggccgcc tggccgtgat ggtcgccgag cgccaggcgc   40020
ccaagatcga ccgcggcgtg tacgacctgg cgcgcgtgct gcgggtgccc ggctcgtaca   40080
accgcaaggg tgagccggtg ctcgtcacgt gtgaacgtgg cggcggtggc ccgctgtcga   40140
tcgaggagct gaccgagcgc ctcaacgagg cgggcgtgcg cgagcaggac ggcgaccggc   40200
gcaccgcgat gggcgaggtt gtgtcgaaac ccgacacctg gaacacgcc gcagctacgt   40260 gcgactattt cgccccgacg atcaaggcgt ggcgcgacga gcagatcacc gagcggcaca   40320
actggctggt gacgcaggcc gtgcggatca tgtgcgggct gcgcaacggc tgcctgactg   40380
aggagcagtt cgagcaggcc cgcaaggtcg tcaccgagcg gttcaaggcc gagtgcgccg   40440
cgaccaaccg ggcgatcccg ccgtgggaga tccccaacgc attcgcctgg gcgaccgatc   40500
```

```
acgcggcccg catgaccgac gccgagctgg cgagcgagat tggcgcgcac ctgcacctgt    40560
gggagaaggc cgagcccgc ccggtgaccc tcgcccccat gcagcccgag caaaccgccg    40620
gcaataccgc aactgtgcag ctcagcgaga taatccgcga gtcgacagct aacgtcacgc    40680
cgaccgatac cggcaacgcc gacctgctcg tcagggcgtg ctcggatcgg ctgcgctggt    40740
gccccgagtc gggcaagtgg ctggtgtgga aaggcacgcg gtggcagccg agcccgacg    40800 gcggcgaggc gatcatggcg gcgatcgagg tcgtgcagtc gatcaaggtc gaggacggcg    40860
acaaggccgg gggccagcac aaaatgcgca gcctgcagcg ccggtcgctc gacaacatgg    40920
tcgcgctcgc caagtgccgc cccggcatgc gcgtgagcct ggccgacctt gacgccgacc    40980
cgtacgcgct gaacaccccg agcggtgtcg tcaacctcaa gacgggcgag ctgacccgc    41040 accgccccga gggctggcac accagggtga cgggcgccgg gtacgagcgc gacggcgcgg    41100
cgccgcggtg gtgggcgttc ctgcaccgca cgttcggcgg cgacaagtcg atggtcgagt    41160
acgtgcaacg gctggccggg tacgcggcga tcgcgaggt gacgcaccac gtgttgccgt    41220
tcctgttcgg cgccgggtcc aacggcaaga gcgtgctcat ggacgtgctc agcgcggtgc    41280
tgggcgacta cgcgatcaca gcgccgggca atttcctgct cgcgggccgg gagcggcacg    41340
aaacggagat agctcgcctg cacggcgccc ggctggtcgt gtgctcggag gtcaacgccg    41400
acagcaagtt cgacgaggcc aaggtcaagc tgctgaccgg cggcgacgtc ctgtcggggc    41460
ggttcatgcg gcaagacttc tttgatttcg tcccgtcgca caccttgttc ctaatgggca    41520
accaccagcc cgatgtgaag gctggcggca cctcattctt tcggcggttc cggctgatcc    41580
cgttcgagca catagtgccc gagcgcgagc gggtcgaggg actggcgcac cagctagtcg    41640
ccgaggaggg cgacgcgatc ctggcgtgga tcgccgacgg cgcccgccag gtgctcgacg    41700
gcggcatgcg ggagcccgcg agcgtgttgg cggctaccgc gcagtaccag gacgacacca    41760
ggaccggcgt cgcccgcttc ctcgacgagt gctgcacgat cggcgagggc gaggccgagg    41820
tcggggcggt gcaccagtgc tatatcgcgt gggccatcgc gcacggtgag ccgctcgtcg    41880
atacggccaa gttcgggcgc gagctgagcg ggaatcaggt cgcccgccgc cgcacggcga    41940
aggcccgcat ggcgaagctg acggttcacg tcgaccggct gccagcaaac ggtgacagca    42000
cctcacccta ccgtcacaac taccgtcacc ccggtgacag tgcaatgacg gatgagtgac    42060
ggacgtatcg acgtgttttc gcaggtagtg acggatatga cggatatgac ggactctcgc    42120
aacattgaaa ctaacatcaa cgcttttgtg tttggtgacc tgcggaaatg ctgcgcggca    42180
gtgctgggtg taacccgtag tgcaaaagtg ccgtcatacc gtcataccc tggcctgcag    42240 caaacaccgc gccgcgcggt ggctcgccgt gtctctcgat tacctcgcgc gcaccggcga    42300
ggccccgaca ccgcacgcaa ctggataggg acaggtgcc catgcaaacc gacgacccgg    42360
tggtcgacga ggcgaagctc gccgcggctg acgctgtgct cgcgatgctg cccgccgacg    42420
cgcacgaggc gctgcgcgag gcgctgcacg cccgcgtgac gggtgaccgt aacggctcac    42480
ggcagttgcg tctgttcgtg ccgggccgcc cggcgccgca gggctcgaaa gacttcaagg    42540
gcttctctaa gacgggcaag gcgatcctca aggagtcgag cgacgccgtc gggccgtggc    42600
gcgagcgtgt ggccctggcc gcggcctcgg cgatcctggc cgaggggctg ccggtgctcg    42660
ccaaagagtt ctcgatcgcc gcgtcggtga cgttcgttat gcctcgcccg gccggggcgc    42720
cgaagcgcag cacgccgccc gccgtgaagc ggcccgacct cgacaagctg gcccgcgcga    42780
tcctcgacgg gctgaccgac gtcgtgtgga tcgacgacag ccaggtcgtc gatttgcact    42840
gccgcaaggt gctggccgag ctgacgcagc cgccgggcgc gcatatccgt atcgcgtcgc    42900
```

-continued

| | | | | |
|---|---|---|---|---|
| cggggctgggg | cgacgaggcg | ctcgcgaagg | ctcaggccgc | ggctcaggcc gcgatcgccg | 42960 |
| ctgccgccga | ggcggtgctg | tgaggcacta | ccgcatcgag | ctgctgatca agtcagacct | 43020 |
| gaccgaggag | caggtcgccg | agcgcgtcga | gggccgtcct | gggccggtgt tcggcggcca | 43080 |
| ggtcgtcgac | gccgcggtgt | acgaggtgac | gcatttcgag | gcgcggcgct cggaggtggt | 43140 |
| cgcgtgagca | ggcaccggca | agaggatcgg | gtgttgcccg | gcccgttcga cccgcggccg | 43200 |
| atcgtggcgt | ggtcggagtc | gatgggctgg | acgcggctgg | aatggatcgc cacgccgacc | 43260 |
| ccgtcgggcg | ggcatctgtg | gctttcggac | gtttgccagc | aagacccggc cgcggccgat | 43320 |
| ccgtgcagct | caggcgacgc | gctcgagttt | ttgccggcgg | ttagctgcgc ccggccgccc | 43380 |
| gagccgatcg | tgacggttta | cgacaaggac | atgcgcaagc | tcgccgggcc tgcgccgtgg | 43440 |
| agccaggtta | ggacgttttt | cgaccatgcg | tgagtgcgcg | aactgcaagg gccgcagcga | 43500 |
| gctgacggtg | tgctggccgt | gcggcaaggc | gatccgccgc | cagctcgtcg gcacggccga | 43560 |
| ggagccgggc | ctcgcgtggc | tgatcgaccg | gctgcaggag | tcggcgtacg gcgaggcgaa | 43620 |
| gatcggccgc | ctggcgccga | aggtgtccgg | tcagggcgag | cggccgggcc tgccgttgaa | 43680 |
| cgcgaaagcg | gccgagctgc | tgcgcgacat | tctgcgcgc | ctgcacaagt ggtccgaggg | 43740 |
| cgcgctgtgg | cgcctgcccg | ccgctgcgca | ggccgcgatg | atggccgaca atgtcccgcg | 43800 |
| gctgatggcc | cgcgacgacg | ccgcggagat | cctgcgcgag | ctgctgcggc tgcgcgccgc | 43860 |
| ggccgagcgg | gcgatcgacc | tgccgcccga | tctgcagtac | gtcggcacgt gcccgagcgt | 43920 |
| gttcgccgac | ggcccgcgca | agggcgaggc | gtgcgctgtg | ggcctgtatg tcgagcgggg | 43980 |
| cgagtcgacg | gtgaactgcc | cgcggtgcaa | gacgccgagc | gtcgtcgagg atctgcagcg | 44040 |
| caccgcgctt | gagcgggtcg | acgacgagcc | caagacggcc | gccgacatgt tccggctgct | 44100 |
| gcggtggctc | gggcgtgagg | tgccgcggtc | gtcgttctat | gtgttggtgc gccgtgtccc | 44160 |
| ggctcgcatg | tatctgcagc | gcgacgggcg | tcggaacatg | ctgcagcagg agggctctca | 44220 |
| gccgctctac | gcctacagcg | acgtcgtgtc | ggccattgac | acgtgggagg ccgagcaggc | 44280 |
| ggcgcagcgg | gccgctggga | agggcaagcg | gggccgccca | cgcaaggcgt cgcccgcggc | 44340 |
| cgaggccaag | cgcgacacgg | tgggcgcagc | gtgttgacag | ctcaacagtg cgcgggtaac | 44400 |
| gtcgccggtg | ttgaccaatc | aacactcggg | ataggagccc | acgaaatgac cgaaatcaca | 44460 |
| gcaggtttgc | gagttcaggt | gttccgcagc | tcgctcggcg | actgcaccaa cggcggcgtg | 44520 |
| accagtaagg | ccgacgtcgt | gacgctgatc | ggctacgccg | accctcacag tggcgccctc | 44580 |
| aagccgctgc | cgcgcatgtc | gcaggtgttc | gagcctgccg | acgacgcccc ggcggtcgtc | 44640 |
| atggtgcgct | cgaacctgcc | cggcgccctg | ccgcacctcg | tgccgctgga cgccaagcag | 44700 |
| gcgggcgagt | ggacgatgca | cggcggcaac | ctggccgggt | cgagcgactc gcggttcggc | 44760 |
| gagctgatcg | agaaggtgtt | cgacggcccg | cgctgcgtta | gctcgctgcc ggtgcacgat | 44820 |
| cggatcgaga | agtgaagcgc | accaggacgg | ttgcggcgcc | cccacctgcg gcgcagcccg | 44880 |
| aggtcgtcgt | gcacggccgc | acgcttgagc | cgggcaccga | ggtgtcgatc cgcggcgagc | 44940 |
| gcggccggtt | ccgctacatg | cgggcgacga | cgacgagcgc | gggccgcctg gtgctcgact | 45000 |
| tcattggcgg | cccggccggg | catgaggcgt | ggcgctcgtt | ttaccccgag cggattcgca | 45060 |
| cggttcaccg | catcaacaaa | acccgccgca | acgcggcctg | attcaagcga ggagacacaa | 45120 |
| acgatgcgca | agtggatagc | gggcaccgcg | gtgggcctgg | tggtcgccct cggggctcag | 45180 |
| gtggccgccg | gtgtcggcat | tgtggtgggc | ctcggccagg | tgccgggcga cttgaacgat | 45240 |

```
ctgcccgagc tgaccgacga ctgaccacca cgaaacgcga aacgccgcag gctgcaacgc    45300
ttgcggcgtt ttcgtgttga caggtcaaca ccacgcatgc ttaactgttg acagctcaac    45360
accgacaccg caagcgcggg gcaaccggcc ccgccccgag cccgaggagg gcctcatgca    45420
caacacccac gtttacggcg agtcggctgt tgagttcgcc gtcggccagc gggtcgcggt    45480
tcacccgatc accccgcagt tcatgcaggg cgaccgttac ggcgaggtcg tgctcgtcgg    45540
ccgcactcgc gtgtcggtga agctcgaccg atcgggtcgc acgctgcggt tctgccgca    45600 gaacctcgcc cacatggccc gcgactagcg ggcctcgggc aggtaatcga acaatcgca    45660 acgggatagg agcccacgag atgaccaacc acatgacacc ggcgcaggcc cgcagaatcg    45720
cgaccgacct gctgcgcgag cacggcctga ccggctggtc tgtcacgttc gacaacgcgc    45780
gacgccgcgc cgggcagtgc agctaccgca cccggcagat cagcctgtcg aaaccgctta    45840
tggcgcagcg gtcctacgac gacaccatga tgacgattac gcacgagctt gcgcacgcgc    45900
tggtcggcgg caggcatggg cacgacgccg tgtgggccgc gaagcaccgc gagctgggcg    45960
gcaacggcaa acggtgcttc gagcacttcg acgagtcggc gccgtggatc ggcacgtgcg    46020
ggcacggcaa gcagttcacc cgctaccgcg ccccgaagcg cctcgacggg tggcgctgcc    46080
gctgcgcccg cggtggctcg ccgatcacgt ggcagacccg cgcgcagcgc gccaccgagg    46140
cccgcgcggt cgcgcaggcg caggcccgca aggtgcccgc accggcggcg gcggccgagg    46200
tgaccccgca gatcgtgtcg cgcccggtcg gccgcgccga gcagctcggg ctgttctgat    46260
gatgaccgac gcagagttcg ccgcccgcct cgacgaaatc gaggcggcgc gcgagcgcga    46320
gtatcaggag cacctggccg ccgagcgcgc caagggcaac cacattcgca agcgggccgg    46380
gcgcagcctg ggcaaccagt ggtacagcca ccagcaccgc gtgcagttca tcgagggtta    46440
cgtcgacccg ctgtcgcaga cgttgtgcgg cgccgacgca acgattttcg accagtcctg    46500
ggccgacacg cggtggccga agcaccgcgc cgaggtcacg tgccaggcgt gcatcgacgc    46560
ccgcctcgcc gacccaaaag cccgccgcta acccacctca caaccaccac aacgggatag    46620
gagcccctgc aatgtccaac cacaccacca cctcggaatc gtcgcccag gaggccgcca    46680 cgcggttctt ttgggcctgg ctgatcgccg ccacggccgc ctcaatcctc gggaacgtca    46740
cgcacgcggt gctcggcgca gccagctcgc cgctgatcgc cgcggcggcg gccatcgtcc    46800
cgccggtcgt gctgctcggc gcgacgcacg gcgtgcacgc cctggtgcgc agccggatcg    46860
tcggcgccgc ctaccgcgcc gccctgacga tcgttgtcgc gcttgcggtg tgcgcgttcg    46920
tgctcagctt cgaggcgctg cgtgagctgg cgatcgtgca cgcgggcatg cggccgtcga    46980
tcgcgtggct gtggccgctg gcaatcgacc tgagcatcac cggctcgacg gttgcgctgc    47040
tggcgctcac cgggcaggct cgcggcgcgc aggcgtacga agtcgagcac ctcgacgcgc    47100
acccgctgtc accgtcgcg cctgtacacg tgtcggtgca caccagcgcg caggcggtcg    47160
cgcaggcggc ggccgtcgac gttgctgagc ccgcaacgga tctgccggtc gaggcggccg    47220
agcggctgct cgacgccggg gtgacgcgca tcgaccgcgt gaaggtcgcc caggtgctcg    47280
ccgagcacgc cgagggcacg gccccgagca tgatcgcgcg caagctgagc gtcgggtaca    47340
gcaccgtggt gcgcatcctt gagcaccaca ctgcgcacgc tgcgcaggcg gatgcggagg    47400
tgggcgcgtg aacgtcgccg agcagtaccc ggcacgcaca gacggcaacg ggcgcacttg    47460
gtttcggccg gtgcgcccgc ccggcgtcga cgtgtcgcaa tggggctgga cgtcgcagcc    47520
cgagcaggct caccccgatt acggcctcgc cgaggtgcgc ccgctgccgg gcggtggcct    47580
ggcagtgctg ccgctggcgg ccccgattta cgagccggtc ggcgagcttg gccccgagtg    47640
```

```
ggtcgacgtc ggagcggtcg agcagtgctg agcgtgcagc ccggcatgaa cgtgccgaag   47700
caacgccgga agatcgagca gcgcctcgtc gaggccccga gcgaggccca tgcgcgttac   47760
ctgcggtggc tgctggcgca gttcgacgag agcctcgccc gcggcctgcc gcgcccggcg   47820
agcgagttcc tgccgatgta cgacgaggag ttcgacccgt agcaaaatgc cggcgagcag   47880
ccgatttgtg cgctgagctg cgcgtcgccg aaaagtcagc aaacgccctg aggcccgcga   47940
ggactcgggg cgtttgtgtt gacacctcaa caccccgcgg tgtagtgttg aggtatcaac   48000
agcacgacgg gataggagcc caaaatgtac aagatgatcg ttcaaatgta cggccgcacc   48060
gaggttaccg agcacgacac gatcgccgag gcccgcgagc gcctggtcac gatcgccgtt   48120
acgcagaact gccgtgtgac cggcgacaac gccaccggcg agttcatcct gcgcgaccgg   48180
gacggcaacg acgacccgcg cgtcacctgg acttacggcg cctaccggat cgaggaggtg   48240
gccgacgtgc gcaccgaggt gatcgtgaag gccgtcgaga acggctgggc cgtcaacgcg   48300
atgcgccccg acttcattca ggccgcccgc ggcaacgtga ccgcgtacgt ggcgctcgac   48360
gccgacggcg gcctcgacac cgccgagctg tacgtcgggc ggcagatcgt cgcctcggcg   48420
tacgccagcg aggacgacgt cgagccgacc ccggcccgcg aggtcgtcgg caactggctg   48480
acgctggccg cctgaccggc gagcacgagg caccccctgag cccgcggtgg ctcgggggc   48540 gctttgtgtt gacacctcaa caggccgcgg tgtactgttg aggtatcaac agcacgaggg   48600
gataggagcc tacaatgtcg aacttcaccg ccgaggaccg cgtcgcgcag accattctcg   48660
accagatcgg tgtcggtacc ctgatgcgcc tgggcgcgca caaggtcgag cgttacctcg   48720
acgccgtcgc gtttcaggtc aagctggcgc tgcccggcca gacccgcggc cggatcatgc   48780
gctgcacgat cgacctcacc gcggccgacc tgtacaacgt caagatcggg ttcctgcagc   48840
gcaagacgct cgattgggtc gcccttgaga acgtcgaggg cgtcgacgtc gagggcatgg   48900
tcacgatcat gcggaagcac gcaaagctga tctgaacgcc agcgcgaagc gcccccgagc   48960
cgatagcggc cggggcgtt ttcgtttgct gtgcacgcgg catgcacgca agcgcagagc   49020
gcgtcgcgca atttagactc ccgattgcag cagcacaact gtgcccaaaa cagcgcgcaa   49080
cccgcgcgag gctgcccaca cgcgcccggc cgaacatgcc agggcgcgtc tgactttcac   49140 gacgggggc gccggtatgc acgtacgcct ggcgatcctc ggcaccgagg tgctgagcct   49200
gcacgtcggc cgcggcctgg tgctcgacgt cgacgccctg ccctcgacg acctcgacga   49260 ggacgacgac cccgagccct gccagctcgt cggcggcggc gcctcgcaca acttcgagcg   49320
cgaccccgac ccgctgagcg ccgacggcga ggtgccgtgg agcgaggccg atttcggatt   49380
cggccggtga ccggcgagcg cctgcggcgc cgcctcgaac tgcgccggtc gaacgccgcg   49440
cagccgcacc gcaaccgaca ccgcgaacgc cagaccgggc aggagcagct cgacgagcca   49500
tgccccgtcg acggccaccc ttgcccctgc gccgccgct accgctgccg ctaagcaccg   49560
cgcatgcacg caggcgccga gcacaccgtg cgccctagcg tcgctcatgt gaccgccgtc   49620
gaggccctga cactggcaat agtgccgcta acgattctcg ttgcggccct tgctgcgtgg   49680
ctggtgaccc gcaaacgcaa ggccgcagcg catccgaccc cggtcgagcg cctcggcggc   49740
ggcatacaca actacccgcc cgactggtgg ctgggcgtcg atcgcccga gtgggactga   49800 gaggagcgac atgctgcaga agatcctgac cggcgtcgct gccgcggtgg ccccggtgat   49860
cgcgaaggcc gtcgccgaga agctcgtcga ggtgctgccc gagctggccg acatcatcgt   49920
gacccggctc gctgagaagc tgcccgacgt cgctgccgcg gtggccgacc gcatcctggc   49980
```

-continued

```
gcacctgccc gacctgtcgg ccctcgacga cgaggcgatc aaggccctgc gtaccctgcc    50040
ggggctgggg gagcacatcg tgcaggccct actcgaccgc ctgccccact ggcccctcaa    50100
gttctaggag taccccgca tggctactcg caccccgcgt gacgcattcg acgctgacac    50160
tgtcgagcag gtcgagcagg acgctgtcga gcaggccgct gagcagcctg ctgacgagtc    50220
aacagcacca gtcgagactg acggcaacgc cgcgcccgag cgcgcggttt acaagccgtt    50280
tgagtggtga gcgaaggtcg caacacagcg cgacgcgatc ggttccgtcg catcattcgc    50340
cgcgacgagc cagactgtca cgtttgcggc gagccaatcg actaccaggc cgaccacctc    50400 gaccogctgt cgttcacgat cgaccacata acgcccttgg ccttgggtgg cactgacacc    50460
ctcgacaaca ttggggcggc tcaccgcaag tgcaaccgcg acaagagcga caagccgccg    50520
agctggcggc cgggcgtcac tttcgtgacc gagcgcgagt ggtagcaaac cgcccggcga    50580
gcgagctcag caaacacgcc ctgacctgcg gttatgcagg ggagtcgagc cagcaaacgc    50640
ccgcggcgcc gatcgagcgc gtttgtgcag gtcagcgacc cctgggggggg tgccccgcga    50700 acgatcgcgg cgcccctcgc ggcat                                          50725
```

MYCOBACTERIUM TUBERCULOSIS ΔESX-3 MUTANTS

CROSS-REFERENCE TO RELATED APPLICATIONS

This application is a U.S. national stage entry under 35 U.S.C. §371 of PCT International Patent Application No. PCT/US2013/040559, filed May 10, 2013, which claims benefit of U.S. Provisional Application No. 61/645,391, filed May 10, 2012, the contents of each of which are incorporated herein by reference into the subject application.

STATEMENT OF GOVERNMENT SUPPORT

This invention was made with government support under grant numbers AI026170 and AI098925 awarded by the National Institutes of Health. The government has certain rights in the invention

BACKGROUND OF THE INVENTION

Throughout this application various publications are referred to by number in parentheses. Full citations for the references may be found at the end of the specification. The disclosures of each of these publications, and also the disclosures of all patents, patent application publications and books recited herein, are hereby incorporated by reference in their entirety into the subject application to more fully describe the art to which the subject invention pertains.

The ESAT-6 gene cluster region 3 ("esx-3 region", namely, Rv0282 through Rv0292 in *Mycobacterium tuberculosis* H37Rv) encodes one of five paralogous Esx (type VII) secretion systems within the *Mycobacterium tuberculosis* genome, and appears to be present in all mycobacterial species sequenced to date (6). Although the specific substrates of this transport system are unknown, extensive previous work, including both saturating transposon mutagenesis studies and attempts to generate deletion mutants through homologous recombination (4-6), has suggested that the esx-3 region of *M. tuberculosis* is essential for growth in vitro and cannot be deleted. In contrast, it is not required for the growth of the saprophytic *mycobacterium M. smegmatis* (e.g. see PCT International Application Publication No. WO 2009/008912, Jacobs et al., published Jan. 15, 2009, hereby incorporated by reference in its entirety). In view of the attenuated virulence and TH1 cytokine profile of *M. smegmatis* Δesx-3 mutants, it would be desirable if a way could be achieved to generate *M. tuberculosis* Δesx-3 mutants.

The present invention address the need for attenuated *M. tuberculosis* mutants and related vaccines based on *M. tuberculosis* Δesx-3 mutants.

SUMMARY OF THE INVENTION

A non-naturally occurring mutant *Mycobacterium tuberculosis* bacterium, wherein the mutant *M. tuberculosis* comprises a deletion in the ESAT-6 gene cluster region 3 (esx-3 region) of a genome of the *M. tuberculosis* bacterium.

The invention also provides a method of producing a mutant *Mycobacterium tuberculosis* bacterium, wherein the mutant *M. tuberculosis* comprises a deletion in the esx-3 region of a genome of the *M. tuberculosis* bacterium, the method comprising deleting a nucleic acid sequence in the esx-3 region of a genome of a *M. tuberculosis* bacterium.

The invention also provides a composition comprising a mutant *Mycobacterium tuberculosis* bacterium, wherein the mutant *M. tuberculosis* comprises a deletion in the esx-3 region of a genome of the *M. tuberculosis* bacterium and a carrier The invention also provides a method of eliciting an immune response in a subject comprising administering to the subject a composition comprising a non-naturally occurring mutant *Mycobacterium tuberculosis* bacterium, or a composition comprising such, wherein the mutant *M. tuberculosis* comprises a deletion in the esx-3 region of a genome thereof, in an amount effective to elicit an immune response.

The invention also provides a non-naturally occurring mutant *Mycobacterium tuberculosis* bacterium, wherein the mutant *M. tuberculosis* comprises a deletion of (i) EsxG, (ii) EsxH, (iii) Esxg and EsxH, (iv) PE5-PPE4, or (v) the four genes PE5 to esxH, of the genome of the *M. tuberculosis* bacterium. The invention also provides a composition comprising such.

The invention also provides a method of eliciting an immune response in a subject comprising administering to the subject a composition comprising a non-naturally occurring mutant *Mycobacterium tuberculosis* bacterium, or the composition comprising such, wherein the non-naturally occurring mutant *M. tuberculosis* comprises a deletion of (i) esxG, (ii) esxH, (iii) esxg and esxH, (iv) PE5-PPE4, or (v) the four genes PE5 to esxH, of a genome of the *M. tuberculosis* bacterium, in an amount effective to elicit an immune response.

Additional objects of the invention will be apparent from the description which follows.

Primer set P4+P5+P6 includes a common right hand primer, P4 (to the right of cloned flank sequences, binding in both wt and mutant), and complementary primers P5 (binds within the esx-3 region, in wild-type only) and P6 (binds to plasmid sequences in mutant only). Finally, primers P7+P8 are within the deleted esx-3 region, and so amplify a product in wild-type only. Schematics of H37Rv wt (A) and H37Rv Δesx-3 (B) chromosomal loci indicate the locations of the three primer sets, and the expected product sizes for wild-type and mutant. C. PCR products using mutant or wild-type genomic DNA as template, or water as negative control, were subjected to agarose gel electrophoresis. Lane designations: 1, H37Rv Δesx-3 clone #1; 2, H37Rv Δesx-3 clone #2; 3, H37Rv Δesx-3 clone #3; wt, H37Rv wt; H₂O, water as negative control.

Figure 4:
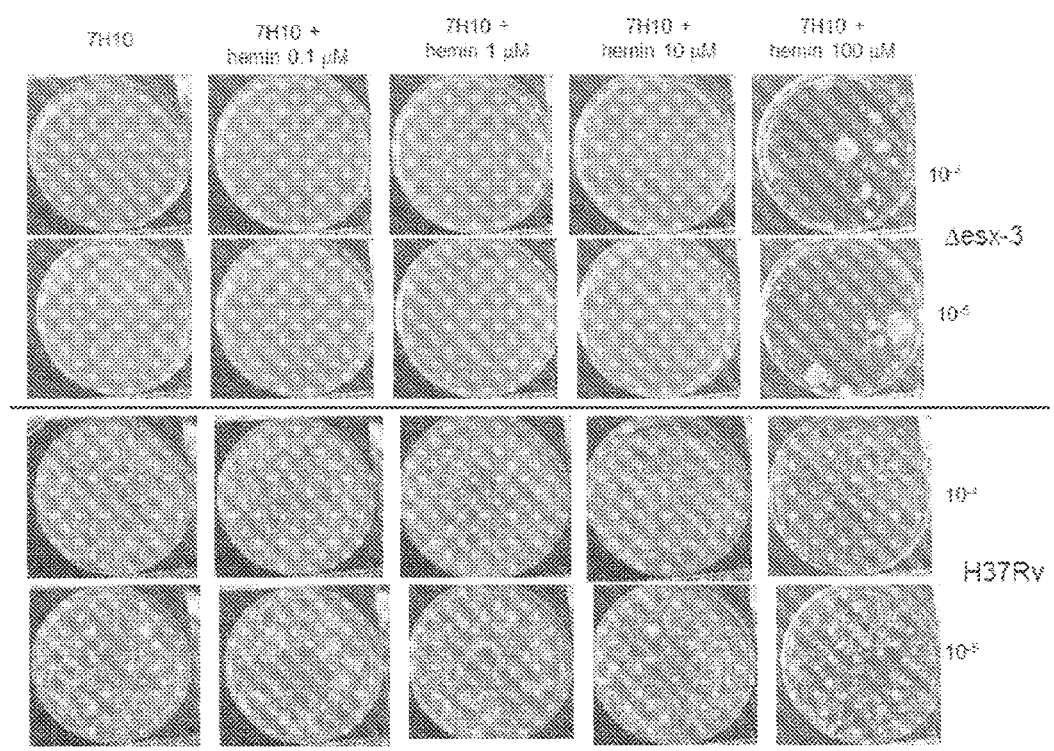

FIG. 4. Hemin enhances the growth of H37Rv Δesx-3 on solid medium. Cultures of H37Rv wt growing in 7H9 liquid medium and H37Rv Δesx-3 growing in 7H9 supplemented with hygromycin 50 µg per ml and hemin (100 µM) were pelleted by centrifugation and washed twice with 7H9+ 0.05% Tween 80 (without supplements), then serially diluted in 7H9+Tween, and 10 µl spots were placed onto 7H10, or 7H10 plus hemin 100 µM and allowed to dry. Plates were photographed after 14 days of incubation at 37° C.

Figure 5:
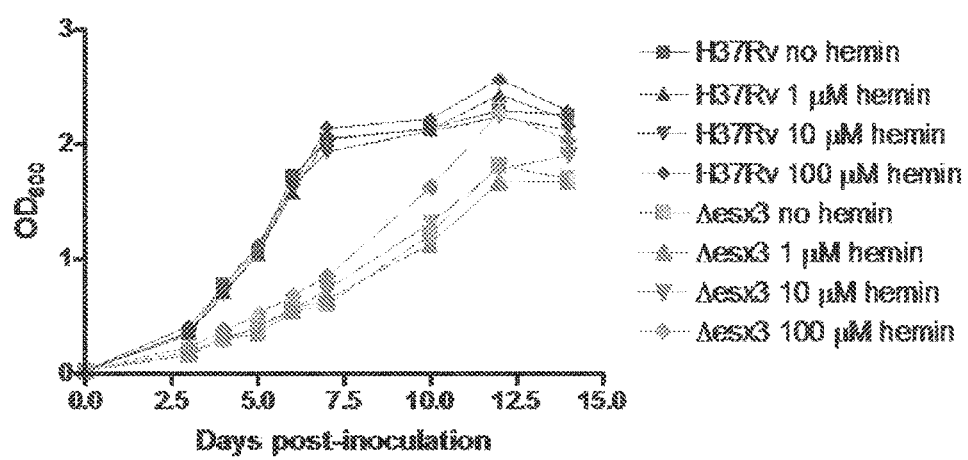

FIG. 5. Hemin enhances growth of H37Rv Δesx-3 in liquid medium. Cultures of H37Rv wt (black symbols) and H37Rv Δesx-3 (gray symbols), both growing in 7H9 medium supplemented with hemin 100 µM (also with hygromycin 50 µg per ml for the esx-3 mutant) were pelleted by centrifugation, washed three times with PBS+tyloxapol 0.05% and resuspended in PBS-tyloxapol, after which each suspension was adjusted to $OD_{600}$=1. Washed bacteria (250 µl) were added to 10 ml of 7H9 complete medium containing tyloxapol 0.05%, either unsupplemented (squares) or supplemented with hemin at 1 (triangles), 10 (inverted triangles) or 100 (diamonds) micromolar. Cultures were incubated with shaking at 37° C., and aliquots were removed at the indicated time points to measure the $OD_{600}$.

Figure 6:
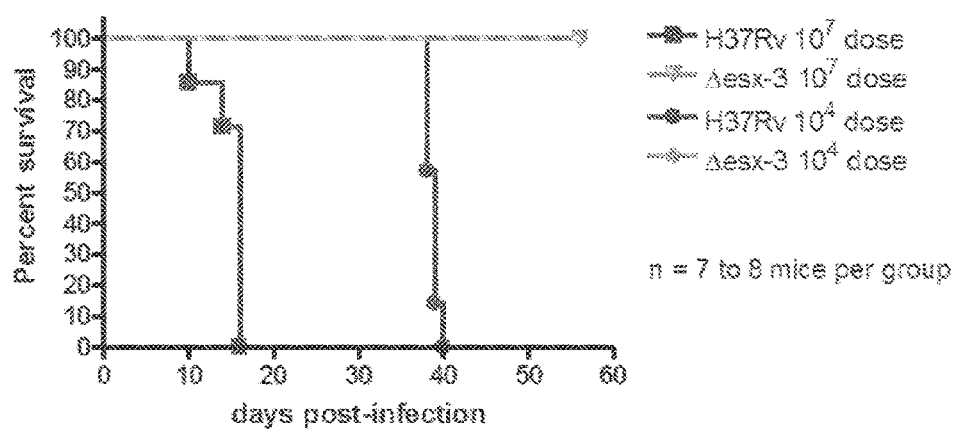

FIG. 6. H37Rv Δesx-3 is significantly attenuated in SCID mice. SCID mice (7-8 mice per group) were injected intravenously via the tail vein with $10^7$ cfu of H37Rv wt (blue squares) or H37RvΔesx-3 (red inverted triangles) or with $10^4$ cfu of H37Rv wt (blue circles) or H37RvΔesx-3 (red diamonds). (cfu estimated by measurement of $OD_{600}$). Prior to injection, bacteria (both wt and mutant) were cultured in 7H9 medium containing tyloxapol 0.05% and hemin 100 µM; medium for the mutant also contained hygromycin 50 µg per ml. Bacteria were washed three times with PBS-0.05% Tween 80 prior to injection. Survival was monitored over time. Actual doses per plating of inocula are indicated.

Figure 7:
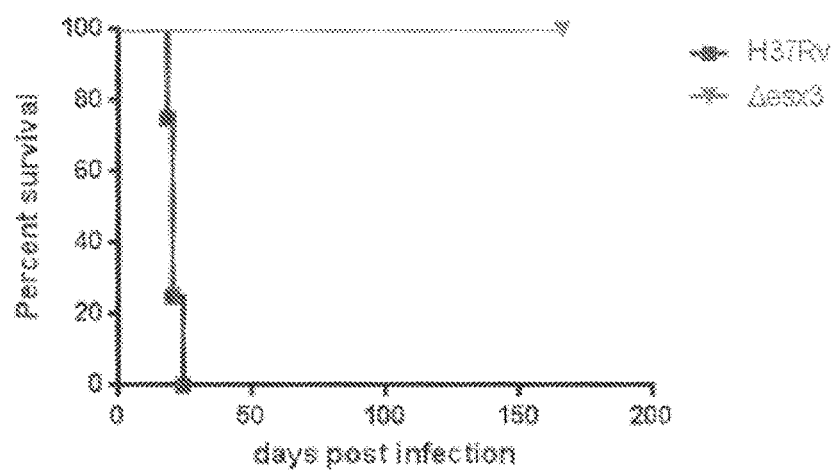
Figure 7:
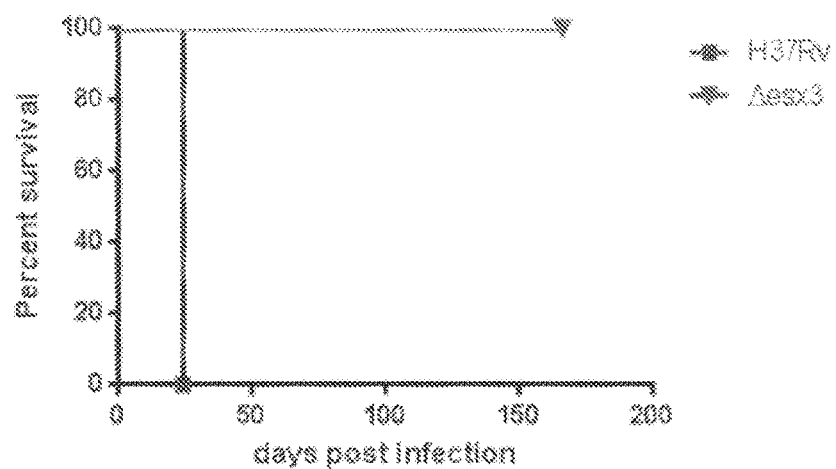

FIG. 7. H37Rv Δesx-3 is also significantly attenuated in RAG(-/-) and MyD88(-/-) mice. RAG(-/-) mice (panel A.) or MyD88(-/-) mice (panel B) were infected intravenously with $10^7$ cfu of H37Rv wt (blue squares) or H37Rv Δesx-3 (red inverted triangles), as described for the infection of SCID mice (FIG. 6). Again, cfu was estimated by measurement of $OD_{600}$. Survival was monitored over time.

Figure 8:
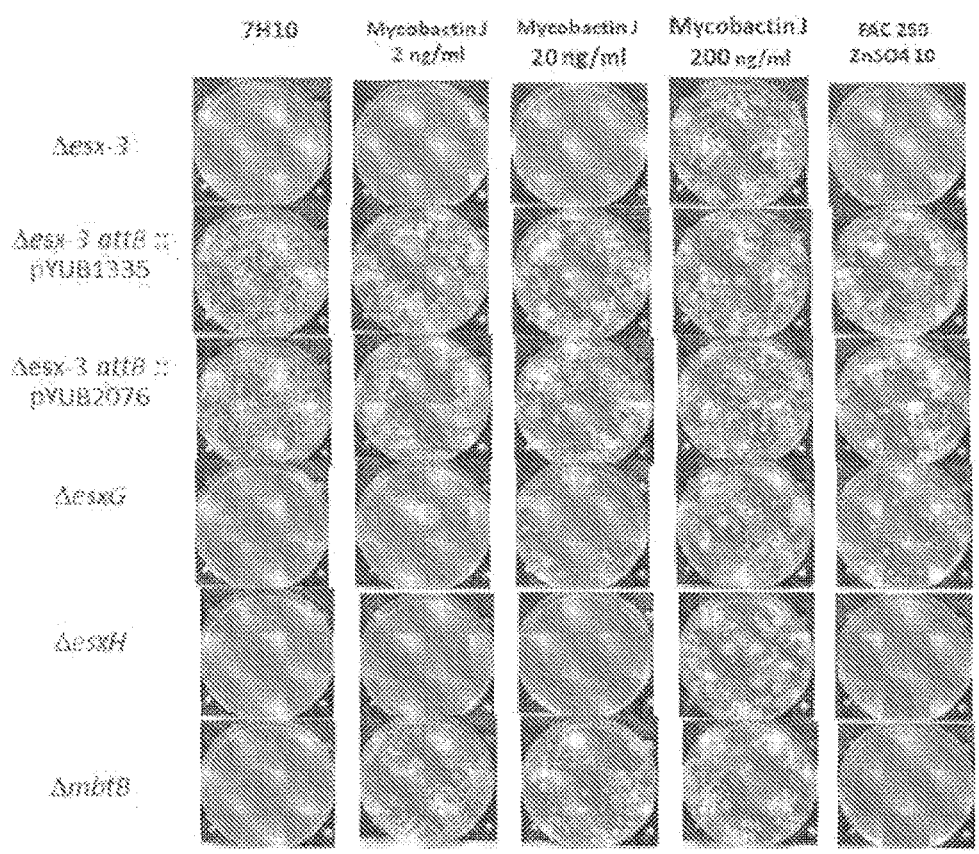

FIG. 8: Mid- to late-log phase cultures of the indicated bacterial strains were washed in PBS+0.05% tyloxapol, resuspended in volumes to give equivalent $OD_{600}$ values, then serially diluted in PBS-tyloxapol to give approximately 300 colonies per 100 µl, and 100 µl aliquots were plated onto each plate. The strains included H37Rv Δesx-3, H37Rv Δesx-3 attB::pYUB1335 (complemented with a cosmid containing the esx-3 region of M. tuberculosis H37Rv), H37Rv Δesx-3 attB::pYUB2076 (complemented with a cosmid containing the paralogous esx-3 region of M. smegmatis), H37RvΔesxG (Rv0287). H37RvΔesxH (Rv0288), and H37RvΔmbtB (Rv2383c). It can be observed that growth of the Δesx-3, ΔesxG and ΔesxH mutants is not supported in 7H10 media, but significant growth is observed on 7H10 media supplemented with mycobactin J (Allied Monitor) at 200 ng/ml. In contrast, the ΔmbtB mutant, predicted from the literature to be deficient in mycobactin synthesis, is able to grow with mycobactin J supplement in amounts as low as 2 ng/ml. The ΔesxG mutant is unique among these mutants in the ability to grow on 7H10 supplemented with additional iron and zinc: in this case ferric ammonium citrate (FAC) at 250 µg/ml and zinc sulfate ($ZnSO_4$) at 10 µg/ml.

Figure 9:
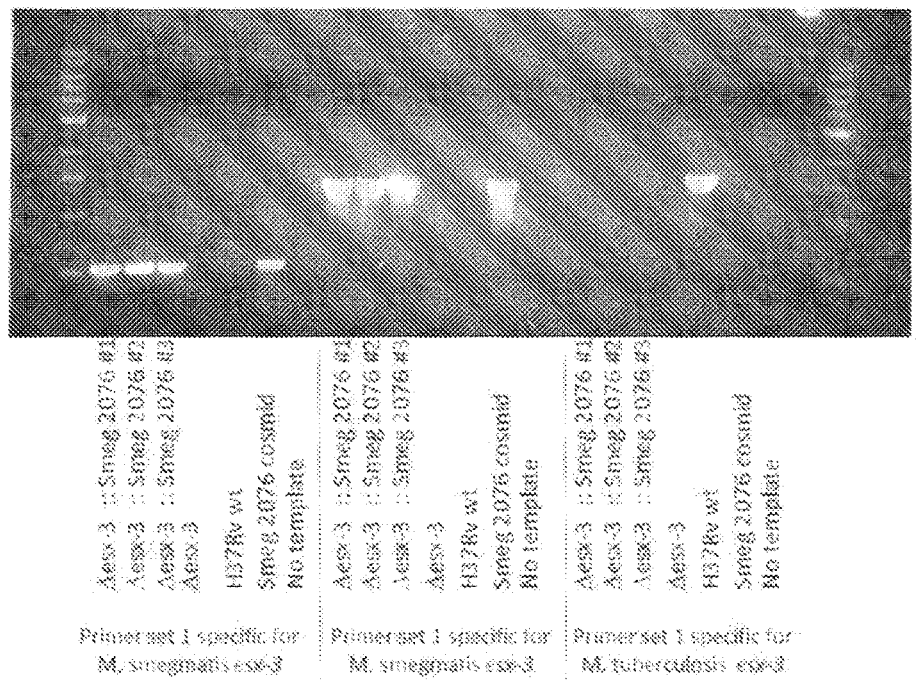

FIG. 9: PCR Screen for H37Rv Δesx-3 complemented with a cosmid encoding the M. smegmatis esx-3 region (pYUB2076).

DETAILED DESCRIPTION OF THE INVENTION

A non-naturally occurring mutant Mycobacterium tuberculosis bacterium, wherein the mutant M. tuberculosis comprises a deletion in the ESAT-6 gene cluster region 3 (esx-3 region) of a genome of the M. tuberculosis bacterium. The non-naturally occurring mutant Mycobacterium tuberculosis bacterium is a mutant by virtue of the deletion in the ESAT-6 gene cluster region 3.

In an embodiment, the M. tuberculosis in which the deletion in the esx-3 region is effected is one of the following: Mycobacterium tuberculosis H37Rv, BTB05-552, BTB05-559, CDC1551, CTRI-2, F11, H37, H37Ra, HN878, KZN 1435, KZN 4207, KZN R506, KZN V2475, R1207, RGTB327, S96-129, X122, '98-R604 INH-RIF-EM', 02_1987, 210, 94_M4241A, C, CDC1551A, CPHL_A, CTRI-4, EAS054, GM 1503, K85, KZN 605, OSDD071, OSDD504, OSDD518, SUMu001, SUMu002, SUMu003, SUMu004, SUMu005, SUMu006, SUMu007, SUMu008, SUMu009, SUMu010, SUMu011, SUMu012, T17, T46, T85, T92, W-148, str. Haarlem, 210_16C10, 210_16C2_24C1, 210_16C2_24C2, 210_32C4, 210_4C15, 210_4C15_16C1, 210_4C15_16C1_48C1, 210_4C15_16C1_48C2, 210_4C15_16C1_56C1, 210_4C15_16C1_56C2, 210_4C31, 210_4C31_16C1, 210_4C31_16C1_24C1, 210_4C31_16C1_40C1, 210_4C31_16C2, 210_8C1, 210_8C6, BC, CTRI-3, H37Rv_2009, NJT210GTG, str. Erdman=ATCC 35801, str. Erdman WHO, CCDC5079, CCDC5180, RGTB423, UT205, CTRI-1, H37RvAE, H37RvCO, H37RvHA, H37RvJO, H37RvLP, H37RvMA, LAM7, NCGM2209, RGTB306, WX1, WX3, XDR1219, XDR1221, str. Beijing/W BT1, or str. Erdman (ATCC 35801). In a preferred embodiment, the M. tuberculosis bacterium is an H37Rv strain. Also provided is a mycobacterium in which the esx-3 region is deleted, wherein the mycobacterium is a M. bovis or M. bovis BCG.

In embodiments the M. tuberculosis in which the esx-3 region deletion is effected is an MDR-TB or an XDR-TB. In embodiments the M. tuberculosis in which the esx-3 region deletion is resistant to, or is suspected of being resistant to kanamycin, isoniazid and/or rifampicin, an aminoglycosides (e.g., amikacin), a polypeptide (e.g., capreomycin, viomycin, enviomycin), a fluoroquinolone, (e.g., ciprofloxacin, levofloxacin, moxifloxacin), and/or a thioamide (e.g. ethionamide).

In an embodiment, the genome in which the deletion is effected has the same sequence as a genome set forth in NCBI Reference Sequence NC_002755.2, NC_009565.1, NC_009525.1, NC_000962.2, NC_012943.1, NZ_ACVS00000000.2, NZ_CM000787.2, CP001662.1, NC_016768.1, NZ_ACVU00000000.2, NZ_CM000789.2, NZ_ACVT00000000.2, NZ_CM000788.2, NC_017026.1, NZ_ABVM00000000.1, NZ_ABLM00000000.1, NZ_ADAB00000000.1, NZ_ABLL00000000.1, NZ_AAKR00000000.1, NZ_AAKR00000000.1, AELF00000000.1, AELF00000000.1, NZ_ABOV0000000.1, NZ_ABQG00000000.1, NZ_AAYK00000000.1, NZ_ACHQ00000000.1, NZ_ABGN00000000.2, NZ_ADHQ00000000.1, NZ_ADHR00000000.1, NZ_ADHS00000000.1, NZ_ADHT00000000.1, NZ_ADHU00000000.1, NZ_ADHV00000000.1, NZ_ADHW00000000.1, NZ_ADHX00000000.1, NZ_ADHY00000000.1, NZ_ADHZ00000000.1, NZ_ADIA00000000.1, NZ_ADIB00000000.1, NZ_ABQH00000000.1, NZ_ACHO00000000.1, NZ_ABOW00000000.1, NZ_ABLN00000000.1, or NZ_AASN00000000.1.

In an embodiment, the deletion comprises less than the complete esx-3 region. In an embodiment, the deletion comprises one or more of genes Rv0282, Rv0283, Rv0284, Rv0285, Rv0286, Rv0287, Rv0288, and Rv0292. In a preferred embodiment, the deletion in the esx-3 region renders the resultant recombinant *M. tuberculosis* less virulent than the wildtype. In an embodiment, the deletion comprises all of genes Rv0282, Rv0283, Rv0284, Rv0285, Rv0286, Rv0287, Rv0288. Rv0289, Rv0290, Rv0291 and Rv0292. In an embodiment, the deletion comprises genes corresponding to Rv0282, Rv0283, Rv0284, Rv0285, Rv0286, Rv0287, Rv0288, Rv0289, Rv0290, Rv0291 and Rv0292. In a preferred embodiment, the mutant *M. tuberculosis* comprises a deletion of the esx-3 region (Rv0282 through Rv0292) of the genome. In an embodiment, the deletion comprises all of genes Rv0282, Rv0283, Rv0284, Rv0285, Rv0286, Rv0287, Rv0288, Rv0289, Rv0290, Rv0291 and Rv0292. In a most preferred embodiment, the deletion of the complete esx-3 region renders the resultant recombinant *M. tuberculosis* less virulent than the wildtype. In an embodiment, the Rv0285 gene is a PE5 gene. In an embodiment, the Rv0286 gene is a PPE4 gene. In an embodiment, the Rv0287 gene is a EsxG gene. In an embodiment, the Rv0288 gene is a EsxH gene. The Rv numbered genes can be identified as set forth in databases of the *Mycobacterium tuberculosis* H37Rv genome (for example, see tuberculist.epfl.ch, genome.tbd-b.org, or see the annotations of the genes as set forth in NCBI Reference Sequence: NC_000962.3).

Further *M. tuberculosis* genome sequences are known in the art and can be found, for example, at Genbank, (www.ncbi.nlm.nih.gov/genbank/). Sequences corresponding to the ESAT-6 gene cluster region 3 (esx-3 region), e.g. identified by Rv0282 through Rv0292 in H37Rv, are readily identifiable by those of ordinary skill in the art, for example by using widely-available sequence alignment software tools. In an embodiment, the invention encompasses recombinant *M. tuberculosis* comprising a deletion in genomic sequences corresponding to the ESAT-6 gene cluster region 3 (esx-3 region).

The non-naturally occurring mutant *Mycobacterium tuberculosis* bacterium may be created so as to comprise further advantageous mutations known in the art that confer reduced virulence, which render the bacterium auxotrophic for an amino acid or for a vitamin (e.g. delta panCD, delta RD1 and delta leuCd mutants), which promote Th1 cytokine profile, and/or which increase the ability of the bacterium to induce apoptosis of a mammalian macrophage. Non-limiting examples of further mutations which can be incorporated into the mutant bacteria of the invention include NuoG mutations, NlaA mutations (see, e.g., US 2010/0297185, Jacobs et al., published Nov. 25, 2010, hereby incorporated by reference), SecA2 mutations (e.g. see U.S. Pat. No. 8,101,191, issued Jan. 24, 2012, Jacobs et al., hereby incorporated by reference) and region of difference 1 (RD1) mutations (e.g. see U.S. Pat. No. 7,722,861, Jan. 24, 2003, Jacobs et al.). In an embodiment, the aforementioned mutants are deletion mutants.

In a preferred embodiment of the mutant bacteria, the non-naturally occurring mutant *Mycobacterium tuberculosis* bacterium is viable, is live and/or is capable or propagating. In an embodiment, the mutant is capable of propagating. In an embodiment, the mutant is capable of propagating in a medium comprising a non-mycobactin dependent source of iron. In an embodiment, the mutant is recoverable in the presence of a non-mycobactin dependent source of iron in its environment for propagation. Examples of non-mycobactin dependent sources of iron are provided herein. In an embodiment, the mutant is capable of propagating in a solid medium comprising a mycobactin wherein the mycobactin is at a concentration of at least 200 ng/ml. In an embodiment, the mutant is not capable of propagating in a solid medium comprising a mycobactin wherein the mycobactin is at a concentration of 2 ng/ml or 20 ng/ml. In an embodiment, the solid media is 7H10 media supplemented with mycobactin J (Allied Monitor).

The mutant *M. tuberculosis* of any of Claims 1-5, wherein the mutant requires for propagation presence either of (i) a non-mycobactin dependent source of iron in its environment, or (ii) a mycobactin source of iron at least 200 ng/ml in its environment.

In an embodiment, the mutant the genome of the mutant is complemented with a nucleic acid sequence identical to an ESAT-6 gene cluster region 3 (esx-3 region) of a genome of *mycobacterium* which is not a *M. tuberculosis*. In an embodiment, the *mycobacterium* which is not a *M. tuberculosis* is a *M. smegmatis*.

A method is provided of producing the mutant *Mycobacterium tuberculosis* bacteria of the invention is also provided. In an embodiment, the mutant *Mycobacterium tuberculosis* bacterium comprising a deletion in the esx-3 region of the genome is made by a method comprising deleting a nucleic acid sequence in the esx-3 region of a genome of a *M. tuberculosis* bacterium by homologous recombination with a non-replicating plasmid which plasmid comprises (i) a nucleic acid sequence identical to a portion of the genome immediately upstream of the deleted nucleic acid sequence and (ii) a nucleic acid sequence identical to a portion of the genome immediately downstream of the deleted nucleic acid sequence, but (iii) no portion identical to the deleted region, in the presence of a non-mycobactin dependent source of iron, or in the presence of a mycobactin dependent source of iron wherein the mycobactin is present at a concentration of 200 ng/ml or greater. In an embodiment, the method is in the presence of a non-mycobactin dependent source of iron.

A method is also provided of producing a mutant *Mycobacterium tuberculosis* bacterium, wherein the mutant *M. tuberculosis* comprises a deletion in the esx-3 region of a genome of the *M. tuberculosis* bacterium, the method comprising deleting a nucleic acid sequence in the esx-3 region of a genome of a *M. tuberculosis* bacterium. In an embodiment, the method comprises effecting deleting the nucleic acid sequence in the esx-3 region of a genome by homologous recombination. In an embodiment, the homologous recombination is performed with a non-replicating plasmid which plasmid comprises (i) a nucleic acid sequence homologous to a portion of the genome immediately upstream of the deleted nucleic acid sequence and (ii) a nucleic acid sequence homologous to a portion of the genome immediately downstream of the deleted nucleic acid sequence, but (iii) no portion identical to the deleted region. In an embodiment, the homologous recombination is performed with a non-replicating plasmid which plasmid comprises (i) a nucleic acid sequence identical in sequence to a portion of the genome immediately upstream of the deleted nucleic acid sequence and (ii) a nucleic acid sequence identical in sequence to a portion of the genome immediately downstream of the deleted nucleic acid sequence. In an embodiment, the method is performed in the presence of a non-mycobactin dependent source of iron. In an embodiment, the method is performed in the presence of a mycobactin dependent source of iron wherein the mycobactin is present at a concentration of 200 ng/ml or greater. In an embodiment of the methods, the method further comprises recovering the mutant M. tuberculosis. In an embodiment of the methods, the method further comprises maintaining the mutant M. tuberculosis in the presence of a non-mycobactin dependent source of iron. In an embodiment of the methods, the method further comprises maintaining the mutant M. tuberculosis in the presence of mycobactin at a concentration of 200 ng/ml or greater.

In an embodiment of the methods, homologous recombination with the non-replicating plasmid is effected by introducing the plasmid into the M. tuberculosis bacterium by way of a transducing phage. Reference (1), the contents of which are hereby incorporated by reference in their entirety, provides an overview of molecular biology techniques that can be employed in the methods herein or producing the mutant M. tuberculosis. In an embodiment, the transducing phage described herein is a mycobacteriophage. As used herein, a "mycobacteriophage" is a phage capable of infecting one or more mycobacteria. Background art for the concept of producing recombinant or mutant mycobacteriophages which may be used in the methods of the invention of producing the mutant M. tuberculosis are discussed in U.S. Pat. No. 6,300,061, and shuttle phasmids are discussed in U.S. Pat. No. 5,750,384, both of which patents are incorporated by reference in their entirety.

In a preferred embodiment of the methods, the transducing phage comprises a phAE159 vector comprising the plasmid sequence. The phage phAE159 is a useful vector for the use in the methods of the invention. The phAE159 has a high cloning capacity and is derived from the temperature sensitive ph101 vector which in turn is derived from TM4. As such, phAE159 is useful as a vector backbone of the invention. In a preferred embodiment, the vector backbone is a phAE159 vector. In an embodiment, the phAE159 vector backbone comprises the sequence set forth in SEQ ID NO:5. In another embodiment, the vector backbone is a ph101 vector. Phages derived from TM4 which are useful as embodiments of the vector backbone in the present invention include, in non-limiting examples, those set forth in Genbank Accession No. JF937104: JF704106: JF704105, HM152764: and HM152767.

In a preferred embodiment of the methods, the non-replicating plasmid further comprises a nucleic acid sequence which provides the recombinant Mycobacterium tuberculosis bacterium with resistance to an anti-bacterial antibiotic. A preferred antibiotic resistance gene is a hygromycin resistance gene. A further example is an ampicillin resistance gene.

In a preferred embodiment of the methods, the genome of the mutant is complemented with a nucleic acid sequence identical to an ESAT-6 gene cluster region 3 (esx-3 region) of a genome of mycobacterium which is not a M. tuberculosis. In an embodiment, the mycobacterium which is not a M. tuberculosis is a M. smegmatis.

In a preferred embodiment of the methods, the non-replicating plasmid further comprises a nucleic acid sequence which encodes a detectable marker. In embodiments, the detectable marker is a β-galactosidase encoded by a LacZ, a maltose binding protein, a chloramphenicol acetyl-transferase, or a fluorescent protein. In an embodiment, the fluorescent protein is a green or yellow fluorescent protein. In a further embodiment, the fluorescent protein is green fluorescent protein derived from A. victoria. Other useful elements, commonly known in the art, may also be included in the genome of the recombinant mycobacteria of the invention. The recombinant mycobacteriophages and vectors of the invention can optionally comprise a mycobacteriophage integration sequence. A sacB gene may be included so as to facilitate unmarking (the sacB gene is from Bacillus subtilis, and is inducible by sucrose and lethal when expressed in Gram-negative bacteria).

In an embodiment of the mutants, compositions, and/or methods, the non-mycobactin dependent source of iron comprises hemin, transferrin, lactoferrin, or ferritin. In a preferred embodiment, the non-mycobactin dependent source of iron comprises hemin. In an embodiment of the mutants, compositions, and/or methods, the non-mycobactin dependent source of iron comprises hemoglobin, whole blood (e.g. blood agar plates), or lysed erythrocytes (e.g. chocolate agar plates). In an embodiment, the methods are performed in the presence of mycobactin or carboxymycobactin. In an embodiment, the mycobactin or carboxymycobactin is present in the media at a concentration of 200 ng/ml or more. In an embodiment, the medium is a solid medium.

In an embodiment of the methods, the concentration of hemin in the culture media in which the mutant Mycobacterium tuberculosis bacteria are maintained is sufficient to maintain viability of the mutant Mycobacterium tuberculosis bacteria. In an embodiment, the concentration of hemin the culture media in which the mutant Mycobacterium tuberculosis bacteria are maintained is in excess of 10 µM. In an embodiment, the concentration of hemin the culture media in which the mutant Mycobacterium tuberculosis bacteria are maintained is in excess of 25 µM, 25 µM-50 µM, 50 µM-75 µM, 75 µM-100 µM, 100 µM-150 µM, 150 µM-200 µM, or in excess of 200 µM. In a preferred embodiment, the concentration of hemin the culture media in which the mutant Mycobacterium tuberculosis bacteria is between 90 µM and 100 µM, is about 100 µM, or is 100 µM.

In an embodiment of the instant method, the sequence homologous to, or identical to, a portion of the genome immediately upstream of the deleted nucleic acid sequence is 825-950 basepairs in length. In a preferred embodiment of the instant method, the sequence is 900 basepairs in length. In an embodiment, the sequence the sequence homologous to, or identical to, a portion of the genome immediately downstream of the deleted nucleic acid sequence is 825-950 basepairs in length. In a preferred embodiment, the sequence is 867 basepairs in length. In an embodiment, the sequence in the plasmid identical to a portion of the genome immediately upstream of the deleted nucleic acid sequence is contiguous with the sequence identical to a portion of the genome immediately downstream of the deleted nucleic acid sequence.

In embodiments, the mutant M. tuberculosis created by the methods described herein is any of the mutant M.

tuberculosis described herein, including, for example, those created so as to comprise further advantageous mutations.

Also provided is a composition comprising a mutant *Mycobacterium tuberculosis* bacterium, wherein the mutant *M. tuberculosis* comprises a deletion in the esx-3 region of a genome of the *M. tuberculosis* bacterium and a carrier. In an embodiment, the carrier is a pharmaceutically acceptable carrier. In an embodiment, the composition further comprises an immunological adjuvant. In an embodiment, the mutant *Mycobacterium tuberculosis* bacterium is live. In an embodiment, the mutant *Mycobacterium tuberculosis* bacterium is capable or propagating. In an embodiment, the carrier comprises a culture media. In an embodiment, the carrier comprises a non-mycobactin dependent source of iron as described herein. In an embodiment, the non-mycobactin dependent source of iron comprises hemin. In an embodiment, the composition is a vaccine composition. In an embodiment, the carrier comprises mycobactin or carboxymycobactin of at least 200 ng/ml.

Compositions are also provided by the invention, comprising any of the mutant *Mycobacterium tuberculosis* bacteria described herein, wherein the mutant *M. tuberculosis* comprises a deletion in the esx-3 region of a genome of the *M. tuberculosis* bacterium and a pharmaceutically acceptable carrier. Pharmaceutically acceptable carriers are known in the art and can be chosen based on intended use. In an embodiment, the genome of the mutant is complemented with a nucleic acid sequence identical to an ESAT-6 gene cluster region 3 (esx-3 region) of a genome of *mycobacterium* which is not a *M. tuberculosis*. In an embodiment, the *mycobacterium* which is not a *M. tuberculosis* is a *M. smegmatis*.

In an embodiment, wherein the composition is intended for administration to a subject, the composition further comprises an immunological adjuvant. Immunological adjuvants encompassed within the compositions and methods of the invention are widely known in the art and include alum, other aluminum salts (e.g. aluminum phosphate and aluminum hydroxide) and squalene. Other immunological adjuvants encompassed within the compositions and methods of the invention include the compounds QS21 and MF59. In an embodiment, the composition is vaccine. In an embodiment, the composition is a live vaccine. In an embodiment, the vaccine comprises a live mutant *Mycobacterium tuberculosis* bacteria described herein. In an embodiment, the vaccine comprises a pharmaceutically acceptable carrier. In an embodiment, the vaccine further comprises an immunological adjuvant.

Any of the compositions of the invention, or any of the mutant *M. tuberculosis* bacteria of the invention, can be used to evoke an immune response in a subject. In an embodiment, administration of a composition of the invention, or the naked mutant *M. tuberculosis* bacteria of the invention, is used to elicit an immune response in the subject. In an embodiment, the eliciting an immune response in a subject is effected by a method comprising administering to the subject a composition comprising a non-naturally occurring mutant *Mycobacterium tuberculosis* bacterium, wherein the mutant *M. tuberculosis* comprises a deletion in the esx-3 region of a genome thereof, in an amount effective to elicit an immune response. In a preferred embodiment, the mutant *M. tuberculosis* comprises a deletion of the esx-3 region (Rv0282-Rv0292) of the genome. In a preferred embodiment, the composition comprises an immunological adjuvant.

The invention also provides a non-naturally occurring mutant *Mycobacterium tuberculosis* bacterium, wherein the mutant *M. tuberculosis* comprises a deletion of (i) EsxG, (ii) EsxH, (iii) Esxg and EsxH, (iv) PE5-PPE4, or (v) the four genes PE5 to esxH, of the genome of the *M. tuberculosis* bacterium. The invention also provides a composition comprising such. In an embodiment the *M. tuberculosis* bacterium is an H37Rv strain. In an embodiment, the mutant further comprises deletion of a gene of the genome involved in amino acid synthesis or involved in vitamin synthesis. In an embodiment, the non-naturally occurring mutant comprises a deletion of a RD1 encoding gene, a LeuCD encoding gene, and/or a panCD encoding gene. A composition comprising the non-naturally occurring mutant of any of Claims 47-49 and a carrier. In an embodiment, the composition is a vaccine composition. In an embodiment, the composition comprises an immunological adjuvant.

The invention also provides a method of eliciting an immune response in a subject comprising administering to the subject a composition comprising a non-naturally occurring mutant *Mycobacterium tuberculosis* bacterium, or the composition comprising such, wherein the non-naturally occurring mutant *M. tuberculosis* comprises a deletion of (i) esxG, (ii) esxH, (iii) esxg and esxH, (iv) PE5-PPE4, or (v) the four genes PE5 to esxH, of a genome of the *M. tuberculosis* bacterium, in an amount effective to elicit an immune response. In an embodiment the *M. tuberculosis* bacterium is an H37Rv strain. In an embodiment, the mutant further comprises deletion of a gene of the genome involved in amino acid synthesis or involved in vitamin synthesis. In an embodiment, the non-naturally occurring mutant comprises a deletion of a RD1 encoding gene, a LeuCD encoding gene, and/or a panCD encoding gene.

In a preferred embodiment of the mutants, compositions and methods of the inventions described herein, the *M. tuberculosis* bacterium is an H37Rv strain. For H37Rv genome, see NCBI Reference Sequence: NC_000962.2, see GenBank: AL123456.2.

The methods disclosed herein involving subjects can be used with any species capable of being infected by *M. tuberculosis*. In a preferred embodiment, the subject is a mammalian subject. Most preferably, the mammal is a human.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Results

Figure 1:
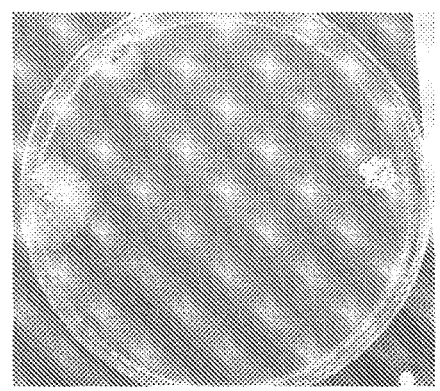
FIG. 1. H37Rv Δesx-3 transductants growing on 7H10 supplemented with hemin 100 μM. *M. tuberculosis* H37Rv was incubated at 37° C. with a specialized transducing phage harboring a construct designed to delete the entire *M. tuberculosis* esx-3 region (Rv0282-Rv0292) and replace the locus with a sacB-hygromycin resistance cassette, as described in the text. Transductions were plated onto 7H10 agar supplemented with hygromycin at 50 micrograms per ml, and hemin at 100 μM. Three colonies were obtained, initially observed at ~4 weeks of incubation at 37° C., and here photographed at ~7 weeks of incubation.

A strategy was investigated for to recovering viable *M. tuberculosis* esx-3 deletion mutants. It was hypothesized that the presence of hemin in the culture media might provide such a route. The entire esx-3 region was deleted from the *M. tuberculosis* H37Rv strain via homologous recombination using specialized transducing phage. The deletion phasmid for the Δesx-3 mutant was constructed by PCR amplification of the 5'-flanking region of Rv0282 using *M. tuberculosis* H37Rv genomic DNA as template with the following primer pairs: esx-3LL 5' TTTTTTTTC-CATAAATTGGTGGCGGCGGGGCTGGACTC 3' (SEQ ID NO:1) and esx-3LR 5' TTTTTTTCCATTTCTTGGC-CACGCCTCCGCTGTCTCCTTC 3' (SEQ ID NO:2). The PCR product was 900 bp. For the 3'-flanking region of Rv0292, the following primer pairs were used: esx-3RL 5' TTTTTTTTCCATAGATTGGGGCTGCACTGGC- CTACTCCTAC 3' (SEQ ID NO:3) and esx-3RR 5' TTTTTTTTCCATCTTTTGG-GCGCCAGCGGTGGAGT-GCATTG 3' (SEQ ID NO:4). This PCR product was 867 bp. Following cloning into plasmid p0004S (esx-3.p0004S) containing the hygromycin resistance cassette and the sacB gene to facilitate unmarking (2), the resulting plasmid was then packaged into the temperature-sensitive phage phAE159, as described earlier (1), to yield the knockout phage for esx-3. Specialized transduction was performed, as described previously (1) and the transduction mix was spread on 7H10 plates, selecting with 50 µg/ml hygromycin. Additionally, plates were supplemented with iron and zinc at various concentrations, and with hemin at 10 µM or 100 µM. After four weeks of incubation at 37° C., colonies were present only on the 7H10 plates supplemented with hemin at 100 µM (FIG. 1).

Figures 2A, 2B, 2C, 2D:
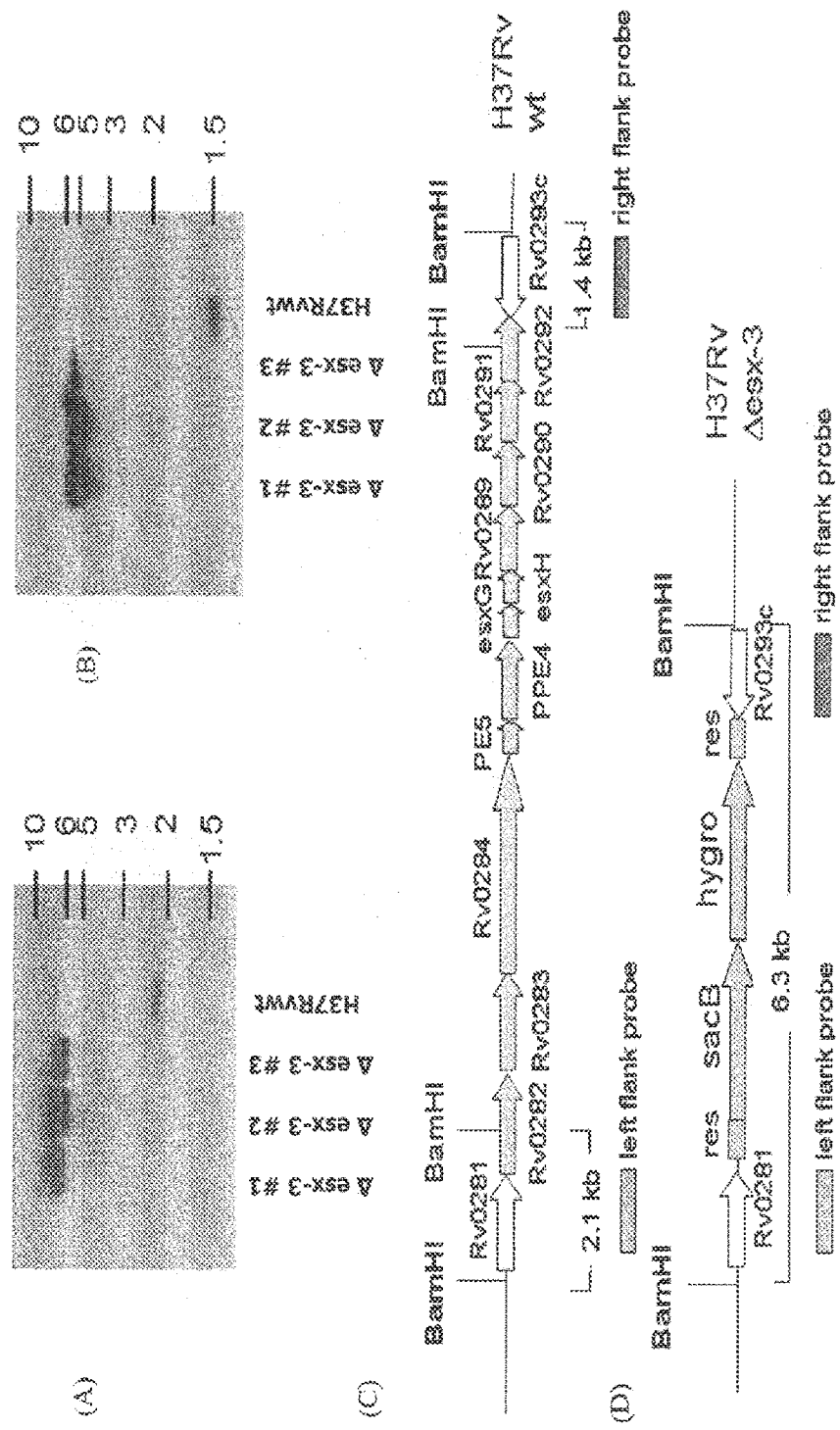
FIGS. 2A-2D. A-B: To confirm that the colonies obtained were esx-3 deletion mutants, genomic DNA was prepared from H37Rv Δesx-3 transductants (#1-#3) and H37Rv wild-type. The DNA was digested with BamHI and, after separation by agarose gel electrophoresis, Southern blots were performed, using as probes sequences immediately flanking the deleted esx-3 region: a 900-bp left flank probe amplified with primers esx-3LL and esx-3LR (A) or a 867-bp right flank probe amplified with primers esx-3RL and esx-3RR (B). In (C) and (D) size differences are the result of elimination of BamHI sites from the chromosome by the extensive deletion, while the inserted sacB-hygromycin resistance cassette contains no BamHI sites (shown schematically).

Confirmation of the successful knockout of the *M. tuberculosis* esx-3 region: To confirm that the colonies obtained were esx-3 deletion mutants, genomic DNA was prepared from H37Rv Δesx-3 transductants (#1-#3) and H37Rv wild-type. The DNA was digested with BamHI and, after separation by agarose gel electrophoresis, Southern blots were performed, using as probes sequences immediately flanking the deleted esx-3 region: a 900-bp left flank probe amplified with primers esx-3LL and esx-3LR (panel A) or a 867-bp right flank probe amplified with primers esx-3RL and esx-3RR (panel B). Analysis of the results demonstrated that both the left and right flank probes hybridized with DNA fragments of sizes expected for the knockout strain and clearly distinct from those expected of the parental strain (FIGS. 2A and 1B). The size differences are the result of elimination of BamHI sites from the chromosome by the extensive deletion, while the inserted sacB-hygromycin resistance cassette contains no BamHI sites (shown schematically in FIGS. 2C and 2D).

Figures 3A, 3B, 3C:
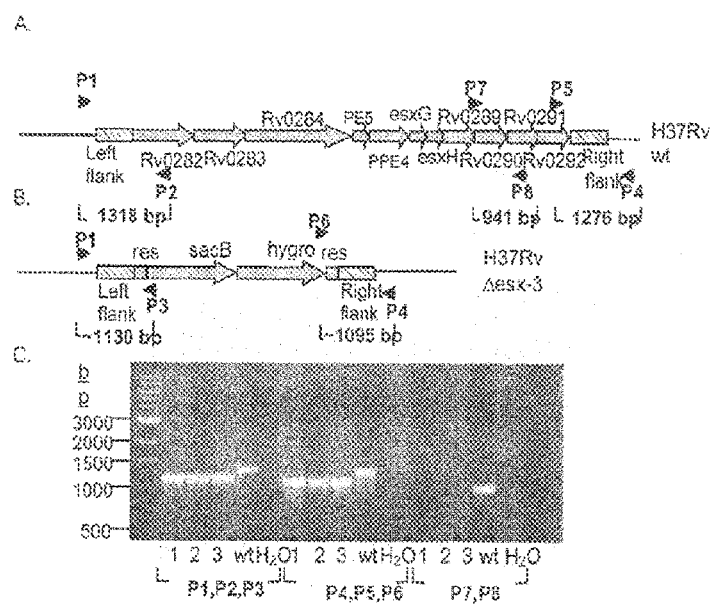
FIG. 3. PCR analysis of H37Rv esx-3 deletion clones. A-B. Genomic DNA prepared from H37Rv Δesx-3 clones, or H37Rv wt, was used as template in PCR reactions to amplify products using three different sets of primers. Primer set P1+P2+P3 includes a common left hand primer, P1 (to the left of flank sequences cloned to make the deletion construct, binding in both wt and mutant), and complementary primers P2 (binds within the esx-3 region, in wild-type only) and P3 (binds to plasmid sequences, in mutant only).

That the recovered colonies were in fact esx-3 deletion mutants was further confirmed by PCR analysis. Genomic DNA was prepared from either the H37Rv Δesx-3 transductants, or from the parental H37Rv wt strain, and was used as template in PCR reactions to amplify products using three different sets of primers (FIG. 3). Primer set P1+P2+P3 includes a common left hand primer, P1, to the left of the cloned flank sequence, binding in both wt and mutant, while complementary primers P2 (specific for wild-type) and P3 (specific for mutant) yield distinct product sizes for mutant and wild-type. Similarly, primer set P4+P5+P6 includes a common right hand primer, P4, to the right of the cloned flank sequence, and complementary primers P5 (specific for wild-type) and P6 (specific for mutant). Finally, primer set P7+P8 includes primers entirely within the deleted esx-3 region, and so amplifies a product in wild-type only. Schematics of H37Rv wt (FIG. 3A) and H37Rv Δesx-3 (FIG. 3B) chromosomal loci indicate the locations of the three primer sets, and the expected product sizes for wild-type and mutant. As shown in FIG. 3C, PCR products confirmed the recovery of the Δesx3 mutants as these samples yielded products corresponding to the expected size for the deletion mutant and a size clearly distinct from that obtained using wild-type genomic DNA. As expected, a water control yielded no product. These data demonstrate that Δesx-3 strains were successfully recovered with the use of hemin supplementation. Subsequent studies demonstrated that mycobactin J at 200 ng/ml or 2000 ng/ml also supports Δesx-3 strain growth on agar. This demonstrates that Δesx-3 strains are viable, in contrast to the current understanding in the art, and that the esx-3 locus appears to be "conditionally essential", and may be deleted when an alternative source of iron (either mycobactin or a non-mycobactin dependent source) is provided.

Growth of the Δesx-3 strain is enhanced in vitro by supplementation of growth medium with hemin: It was hypothesized that an *M. tuberculosis* Δesx-3 strain would exhibit impaired growth in the absence of hemin. As noted, following transduction H37Rv Δesx-3 colonies were obtained on 7H10 agar supplemented with hemin at 100 µM (FIG. 1) at 4 weeks of incubation, but not on 7H10 lacking hemin (not shown). Once the mutants were obtained and confirmed, studies were undertaken to further explore the effect of hemin on growth. The H37Rv Δesx-3 strain, cultured in the presence of hemin 100 µM, was washed, diluted and plated onto 7H10 agar with and without hemin, in comparison with the H37Rv wt parental strain. Hemin was demonstrated to enhance growth of the Δesx-3 strains relative to the parental strain on solid medium 7H10 (FIG. 4). Similarly, growth in liquid 7H9 medium was also enhanced by supplementation with hemin at the highest concentration studied, 100 µM (FIG. 5). The fact that growth is seen in liquid media even in the absence of hemin (as well as on solid media at lower dilutions—not shown) may be due to carryover of hemin from the original culture medium, or perhaps to intracellular storage of iron. A similar phenomenon has been observed by others for *M. bovis* BCG mutants in the mycobactin synthesis pathway, which are able to grow for some generations in the absence of exogenous mycobactin—the higher the concentration of mycobactin in the original culture medium, the more growth (doublings) is observed in the absence of mycobactin (8). Similarly, growth in liquid 7H9 medium was also enhanced by supplementation with hemin at the highest concentration studied, 100 µM (FIG. 5). Again, growth is observed in the absence of exogenous hemin, equivalent to ~6 doublings (from $OD_{600}$~0.025 to $OD_{600}$~1.6), perhaps due to the intracellular storage issues mentioned above. The 7H9 medium used in these studies is also complex, containing BSA supplementation which may potentially contain some heme.

Using specialized transduction, we have generated strains deleted for esxG (Rv0287) and esxH (Rv0288). Like the Δesx-3 strain, these mutants grow when provided supplemental mycobactin J (FIG. 8). These data demonstrate that loci within the Esx3 region that do not encompass the entire Esx3 region are also conditionally essential. Utilizing specialized transduction, we have also generated strains harboring combined deletions of esxG-esxH (Rv0287-Rv0288) and PE5-PPE4 (Rv0285-Rv0286), and PE5 through esxH (Rv0285-Rv0288) and were able to recover the deletion mutants on medium supplemented with mycobactin J at 2000 ng/ml.

The Δesx3 strain is highly attenuated following iv inoculation into SCID mice, RAG(−/−) mice and MyD88 (−/−) mice: The esx-3 region of the soil-dwelling organism *Mycobacterium smegmatis* has recently been deleted from the chromosome, and the resulting strain complemented by chromosomal integration of the orthologous *M. tuberculosis* esx-3 region (6). This yielded the IKEPLUS strain, named for its phenotypes with respect to "Immune Killing Evasion" (6). *M. smegmatis* IKEPLUS was found to be significantly attenuated (similar to the parental *M. smegmatis* Δesx-3 IKE strain from which it derived), and additionally was found to induce a highly potent T helper type I ($T_H1$) cytokine response in infected mice, with enhanced production of IL-12 and IFN-γ, and very low IL-6 compared with wild-type *M. smegmatis*. As predicted from this cytokine milieu, which should provide efficient priming of $T_H1$ cell responses, IKEPLUS was found to be a highly effective vaccine against challenge with virulent *M. tuberculosis*. Mice vaccinated with IKEPLUS exhibited prolonged survival following *M. tuberculosis* challenge, as compared with BCG-vaccinated mice, and IKEPLUS vaccination also induced significant declines in bacterial burdens in the tissues of mice surviving to later time points after challenge, declines which in some cases exceeded by 3 logs those seen in BCG-immunized mice, and in one experiment actually resulted in sterilizing immunity. The *M. tuberculosis* genes present in IKEPLUS were essential to produce this highly effective immune response, as protection was much more modest with the parental IKE strain, with survival and bacterial burden similar to naïve mice (6).

Given the above summarized findings regarding attenuation of the IKE and IKEPLUS strains, the virulence of the H37Rv Δesx-3 strain was assessed. SCID mice (7 to 8 per group) were infected intravenously with a high dose, $10^7$ (by $OD_{600}$ estimate), of wasH37hed bacilli, and survival was monitored over time (FIG. 6). Very significant attenuation of the Δesx-3 strain was apparent, as all of the H37Rv wild-type-infected mice succumbed to the infection within 16 days, while all Δesx-3-infected mice remain alive and without signs of illness at >50 days after infection.

The *M. tuberculosis* Δesx-3 strains disclosed herein can be used in live attenuated tuberculosis vaccines and also as the backbone for live attenuated tuberculosis vaccines which include additional attenuating and/or immunomodulatory mutations. The H37Rv Δesx3 strain was used to subcutaneously vaccinate immunocompetent C57BL/6 mice at a dose of $10^6$/mouse. Controls included unvaccinated (Naïve) animals and animals vaccinated with BCG, and another candidate vaccine strain H37Rv ΔleuDpanCDsecA2. The animals were challenged by low dose aerosol infection with *M. tuberculosis* Erdman strain at two months post vaccination Bacterial burdens in lung and spleen were determined at 1, 3 and 5 months post-challenge (Table 1). In addition, animals were challenged 6 months post-vaccination and lung and spleen titers were determined one month post-challenge (Table 1). At all time points examined, the Δesx-3 vaccine reduced lung titers by a statistically-significant amount. In addition, Δesx-3 vaccine reduced spleen titers to a statistically-significant degree in the spleen at one month post-challenge in animals challenged either one or six months after vaccination. These data support the use of Δesx-3 as a vaccine or as a backbone for a vaccine.

FIG. 8 shows Mid- to late-log phase cultures of the indicated bacterial strains were washed in PBS+0.05% tyloxapol, resuspended in volumes to give equivalent $OD_{600}$ values, then serially diluted in PBS-tyloxapol to give approximately 300 colonies per 100 μl, and 100 μl aliquots were plated onto each plate. The strains included H37Rv Δesx-3, H37Rv Δesx-3 attB::pYUB1335 (complemented with a cosmid containing the esx-3 region of *M. tuberculosis* H37Rv), H37Rv Δesx-3 attB::pYUB2076 (complemented with a cosmid containing the paralogous esx-3 region of *M. smegmatis*), H37RvΔesxG (Rv0287), H37RvΔesxH (Rv0288), and H37RvΔmbtB (Rv2383c). It can be observed that growth of the Δesx-3, ΔesxG and ΔesxH mutants is not supported in 7H10 media, but significant growth is observed on 7H10 media supplemented with mycobactin J (Allied Monitor) at 200 ng/ml. In contrast, the ΔmbtB mutant, predicted from the literature to be deficient in mycobactin synthesis, is able to grow with mycobactin J supplement in amounts as low as 2 ng/ml. The ΔesxG mutant is unique among these mutants in the ability to grow on 7H10 supplemented with additional iron and zinc: in this case ferric ammonium citrate (FAC) at 250 μg/ml and zinc sulfate ($ZnSO_4$) at 10 μg/ml.

FIG. 9 shows a PCR Screen for H37Rv Δesx-3 complemented with a cosmid encoding the *M. smegmatis* esx-3 region (pYUB2076).

TABLE 1

Bacterial burden ($log_{10}$ cfu) in lung and spleen after subcutaneous vaccination with the indicated strains followed by aerosol challenge with *M. tuberculosis* Erdman strain.

| Experimental Group | Lung | Spleen |
|---|---|---|
| 2 months post-vaccination, 1 month post-challenge | | |
| Naive | 5.88 ± 0.05 | 5.00 ± 0.06 |
| BCG | 5.02 ± 0.06* | 4.14 ± 0.04* |
| ΔleuDpanCDsecA2 | 5.48 ± 0.10* | 4.61 ± 0.14* |
| Δesx-3 | 4.86 ± 0.11* | 4.03 ± 0.13* |
| 2 months post vaccination, 3 month post challenge | | |
| Naive | 5.31 ± 0.20 | 4.71 ± 0.25 |
| BCG | 4.83 ± 0.26* | 4.01 ± 0.61 |
| ΔleuDpanCDsecA2 | 5.22 ± 0.12 | 4.67 ± 0.17 |
| Δesx-3 | 4.82 ± 0.25* | 4.73 ± 0.44 |
| 2 months post vaccination, 5 months post challenge | | |
| Naive | 5.44 ± 0.16 | 4.41 ± 0.08 |
| BCG | 5.15 ± 0.16 | 4.34 ± 0.04 |
| ΔleuDpanCDsecA2 | 5.36 ± 0.14 | 4.36 ± 0.03 |
| Δesx-3 | 5.04 ± 0.07* | 4.27 ± 0.14 |
| 6 months post vaccination, 1 month post challenge | | |
| Naive | 5.88 ± 0.03 | 4.62 ± 0.06 |
| BCG | 4.91 ± 0.03* | 4.15 ± 0.09* |
| ΔleuDpanCDsecA2 | 5.04 ± 0.03* | 4.16 ± 0.04* |
| Δesx-3 | 4.72 ± 0.14* | 4.08 ± 0.03* |

*Statistically different than naïve controls ($p < 0.05$)

REFERENCES

1. Bardarov, S., S. Bardarov Jr, Jr., M. S. Pavelka Jr, Jr., V. Sambandamurthy, M. Larsen, J. Tufariello, J. Chan, G. Hatfull, and W. R. Jacobs Jr, Jr. 2002. Specialized transduction: an efficient method for generating marked and unmarked targeted gene disruptions in *Mycobacterium tuberculosis*, *M. bovis* BCG and *M. smegmatis*. Microbiology 148:3007-17.
2. Dao, D. N., K. Sweeney, T. Hsu, S. S. Gurcha, I. P. Nascimento, D. Roshevsky, G. S. Besra, J. Chan, S. A. Porcelli, and W. R. Jacobs. 2008. Mycolic acid modification by the mmaA4 gene of *M. tuberculosis* modulates IL-12 production. PLoS Pathog 4:e1000081.
3. Jones, C. M., and M. Niederweis. *Mycobacterium tuberculosis* can utilize heme as an iron source. J Bacteriol 193:1767-70.
4. Sassetti, C. M., D. H. Boyd, and E. J. Rubin. 2003. Genes required for mycobacterial growth defined by high density mutagenesis. Mol Microbiol 48:77-84.
5. Siegrist, M. S., M. Unnikrishnan, M. J. McConnell. M. Borowsky, T. Y. Cheng, N. Siddiqi, S. M. Fortune, D. B. Moody, and E. J. Rubin. 2009. Mycobacterial Esx-3 is required for mycobactin-mediated iron acquisition. Proc Natl Acad Sci USA 106:18792-7.
6. Sweeney, K. A., D. N. Dao, M. F. Goldberg, T. Hsu, M. M. Venkataswamy, M. Henao-Tamayo, D. Ordway, R. S. Sellers, P. Jain, B. Chen, M. Chen, J. Kim, R. Lukose, J. Chan, I. M. Orme, S. A. Porcelli, and W. R. Jacobs, Jr. A recombinant *Mycobacterium smegmatis* induces potent bactericidal immunity against *Mycobacterium tuberculosis*. Nat Med 17:1261-8.

7. Tullius, M. V., C. A. Harmston, C. P. Owens. N. Chim, R. P. Morse, L. M. McMath, A. Iniguez, J. M. Kimmey, M. R. Sawaya, J. P. Whitelegge, M. A. Horwitz, and C. W. Goulding. Discovery and characterization of a unique mycobacterial heme acquisition system. Proc Natl Acad Sci USA 108:5051-6.

8. Tullius, M. V., G. Harth, S. Maslesa-Galic, B. J. Dillon, and M. A. Horwitz. 2008. A Replication-Limited Recombinant *Mycobacterium* bovis BCG vaccine against tuberculosis designed for human immunodeficiency virus-positive persons is safer and more efficacious than BCG. Infect Immun 76:5200-14.

What is claimed:

1. A method of eliciting an immune response in a subject comprising administering to the subject a composition comprising a non-naturally occurring mutant *Mycobacterium tuberculosis* bacterium, wherein the mutation of the mutant *M. tuberculosis* consists of a deletion of the entire esx-3 region of a genome thereof, in an amount effective to elicit an immune response.

2. The method of claim 1, wherein the mutant *M. tuberculosis* is administered as a composition comprising the mutant *Mycobacterium tuberculosis* bacterium and a carrier.

3. The method of claim 2, wherein the carrier is a pharmaceutically acceptable carrier.

4. The method of claim 2, wherein the composition further comprises an immunological adjuvant.

5. The method of claim 1, wherein the mutant *Mycobacterium tuberculosis* bacterium is live.

\* \* \* \* \*